(12) United States Patent
Peglion et al.

(10) Patent No.: US 6,903,103 B2
(45) Date of Patent: Jun. 7, 2005

(54) LINEAR CYCLIC UREAS

(75) Inventors: Jean-Louis Peglion, Le Vesinet (FR); Christophe Poitevin, Paris (FR); Jean-Paul Vilaine, Chatenay-Malabry (FR); Nicole Villeneuve, Rueil-Malmaison (FR); Marie-Pierre Bourguignon, Chatou (FR); Catherine Thollon, Paris (FR)

(73) Assignee: Les Laboratories Servier, Nueilly-sur-Seine (FR)

( * ) Notice: Subject to any disclaimer, the term of this patent is extended or adjusted under 35 U.S.C. 154(b) by 51 days.

(21) Appl. No.: 10/369,860

(22) Filed: Feb. 20, 2003

(65) Prior Publication Data

US 2003/0229100 A1 Dec. 11, 2003

Related U.S. Application Data

(62) Division of application No. 09/751,716, filed on Dec. 29, 2000, now Pat. No. 6,566,364.

(30) Foreign Application Priority Data

Dec. 30, 1999 (FR) ............................................. 99 16701

(51) Int. Cl.$^7$ .................... C07D 401/04; C07D 401/08; C07D 403/04; A61K 31/496; A61P 9/10
(52) U.S. Cl. ............................ 514/253.05; 514/253.05; 514/253.06; 514/253.07; 514/307; 514/314; 546/146; 546/148; 546/150; 546/165; 546/166; 546/139; 546/153; 546/168; 546/169; 544/363
(58) Field of Search ........................ 544/363; 546/146, 546/148, 150, 166, 165, 168, 169, 139, 153; 514/253.05, 253.06, 253.07, 307, 314

(56) References Cited

PUBLICATIONS

AHA Medical/scientific Statement (Herbert C. Stary et al.) (http:/216.185.102.50/Scientific&statements/1995/ 179500005.html).*
Candipan RC, et al. Arterioscler. Thromb. Vasc. Biol. 1996, 16, 44–50.
Cooke JP, et al. J. Clin. Invest. 1992, 90, 1168–1172.
Dillon GA, et al. Contemporary cardiology, vol. 4: Nitric oxide and the Cardiovascular System. Edited by Loscalzo J. and Vita J.A., 2000, 13, 207–225.
Eberhardt RT, et al. Contemporary cardiology, vol. 4: Nitric oxide and the Cardiovascular System. Edited by Loscalzo J. and Vita J.A., 2000, 13, 273–295.
Kauser K, et al. Am. J. Physiol. 2000, 278, H1679–H1685.
Ludmer PL, et al. N. Engl J. Med. 1986, 315, 1046–1051.
Napoli C, et al. Nitric Oxide 2001, vol. 5, No 2, 88–97.
Naruse K, et al. arterioscler. Thromb. 1994, 14, 746–752.
Schachinger V, et al. coronary Artery Disease 2001, vol. 12, No6, 435–443.
Wang BY, et al. J. Am. Coll. Cardiol. 1994, 23, 452–458.
Zeiher AM, et al. Circulation, 1991, 83, 391–401.

* cited by examiner

Primary Examiner—Mukund J. Shah
Assistant Examiner—Kahsay Habte
(74) Attorney, Agent, or Firm—The Firm of Hueschen and Sage

(57) ABSTRACT

Compound of formula (I):

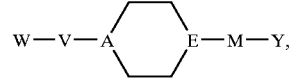

(I)

wherein:
V represents a single bond or an alkylene chain,
M represents a single bond or an alkylene chain,
A and E each represents nitrogen or CH, but at least one of the two groups A or E represents nitrogen,
W represents a group of formula (i), (ii) or (iii):

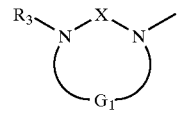

(i)

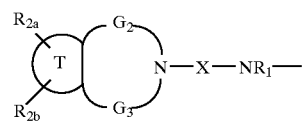

(ii)

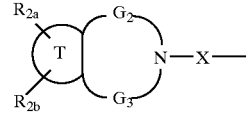

(iii)

wherein:
X represents carbonyl, sulphonyl or sulphoxide,
$G_1$, $G_2$ and $G_3$ are as defined in the description,
T represents a fused phenyl group or a fused pyridyl group,
$R_1$ represents hydrogen, linear or branched $(C_1-C_6)$alkyl, aryl or aryl-$(C_1-C_6)$alkyl in which the alkyl moiety is linear or branched,
$R_{2a}$ and $R_{2b}$, which are the same or different, are as defined in the description,
$R_3$ represents aryl or heteroaryl-A as defined in the description, each of which groups may optionally be substituted,
Y represents aryloxy, heteroaryloxy or heteroaryl-B as defined in the description, each of which groups may optionally be substituted,
its isomers, its hydrates, its solvates and addition salts thereof with a pharmaceutically acceptable acid.

Medicinal products containing the same which are useful in the treatment of diseases or pathological conditions in which endothelial dysfunction is known.

13 Claims, No Drawings

LINEAR CYCLIC UREAS

This application is a divisional of Ser. No. 09/751,716 filed on Dec. 29, 2000, now U.S. Pat. No. 6,566,364.

BACKGROUND OF THE INVENTION

The compounds of the present invention are useful in the treatment of diseases or pathological conditions in which endothelial dysfunction is known to be a pathogenic and/or aggravating mechanism. Such pathologies are: atherosclerosis, the existence of vascular risk factors (dyslipidaemia, diabetes, systemic arterial hypertension), the various clinical forms of myocardial or peripheral ischaemia, cardiac insufficiency and the various forms of pulmonary arterial hypertension. The said compounds are also useful in the treatment of patients undergoing heart transplantation or vascular repermeabilisation such as a bypass, thrombolysis or arterial dilatation with or without a stent.

A reduction in the vascular availability of nitrogen monoxide (NO) constitutes the major mechanism of endothelial dysfunction observed in the diseases and pathological conditions mentioned above and explains its pathogenic role (*Cardiovasc. Res.*, 1999, 43, 572; *Coronary. Art. Dis.* 1999, 10, 277; *Coronary. Art. Dis.*, 1999, 10, 301; *Coronary. Art. Dis.*, 1999, 10, 287; *Coronary. Art. Dis.*, 1999, 10, 295).

In the said pathological conditions, the endothelial dysfunction may in fact result from two main mechanisms: 1) inadequate production of NO associated with inhibition of endothelial NO synthase by endogenous inhibitors such as ADMA (asymmetric dimethyl-arginine), the plasma concentration of which increases in patients exhibiting cardiovascular risk factors (*Cardiovasc. Res.*, 1999, 43, 542; *Hypertension*, 1997, 29, 242; *Circulation*, 1997, 95, 2068), 2) inactivation of the NO by the superoxide anion ($O_2^-$), the production of which is increased in pathological conditions (*Cardiovasc. Res.*, 1999, 43, 562; *Eur. J Biochem.* 1997, 245, 541; *J. Clin. Invest.*, 1993, 91 2546).

Under normal conditions, NO produces major effects such as: 1) regulation of arterial vasomotricity by means of its vasodilator effect (*N Engl. J Med.*, 1993, 329, 2002; *Nature*, 1980, 288, 373), 2) limitation of platelet adhesion and aggregation (*Trends Pharmacol. Sci.*, 1991, 12, 87), 3) control of the adhesion of leukocytes and monocytes to endothelial cells (*Proc. Natl Acad. Sci. USA*, 1991, 88, 4651), 4) inhibition of the proliferation of vascular smooth muscle cells (*Cardiovasc. Res.*, 1999, 43, 580, *Circulation*, 1993, 87 V51), which explains why the deficiency of NO in the arterial wall is favourable to pathological phenomena such as vasoconstriction, thrombosis, lipid accumulation and proliferation of vascular smooth muscle cells.

In vitro experiments have enabled it to be shown that the compounds of the present invention are capable of limiting the endothelial dysfunction and reduced vascular availability of NO that are caused by tests involving the two physiopathological mechanisms already mentioned: inhibition of endothelial NO synthase and oxidative stress due to production of $O_2^-$.

Besides the fact that they are new, the compounds of the present invention, by virtue of their specific pharmacological activity, which is capable of limiting the development of endothelial dysfunction, are useful in preventing the development, extension and complications of atherosclerotic lesions, especially in patients exhibiting a vascular risk factor (dyslipidaemia, diabetes, arterial hypertension), and in treating the various clinical forms of myocardial or peripheral ischaemia, cardiac insufficiency and the various forms of pulmonary arterial hypertension. The compounds are also used for preventing vascular complications (spasm, thrombosis, restenosis, accelerated atherosclerosis) in patients undergoing a bypass, vascular dilatation with or without a stent or other forms of vascular repermeabilisation and also heart transplantation.

DESCRIPTION OF THE PRIOR ART

Compounds of similar structure have been described in the literature, that being the case, more especially, for Patent Application WO 94/13659, which claims compounds containing especially a cyclic urea structure, those compounds being useful in the treatment of diseases of the central nervous system such as depression or psychosis. Similarly, Patent Specification FR 2 338 940 describes compounds containing especially a 1-{1-[2-hydroxy-3-(aryloxy)-propyl]4-piperidyl}-3-aryl-imidazolidin-2-one structure and claims them for their usefulness in the treatment of vascular hypertension. Finally, Patent Specification EP 0 526 342 describes new (isoquinolin-5-yl)sulphonamides, which are useful in the treatment of myocardial ischaemia.

The compounds of the present invention are clearly distinguished from that prior art, both in their particular chemical structure and in their specific pharmacological activity of endothelial protection.

DETAILED DESCRIPTION OF THE INVENTION

More specifically, the present invention relates to compounds of formula (I):

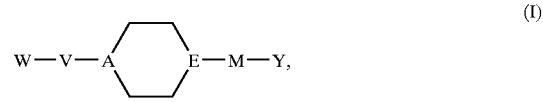

(I)

wherein:

V represents a single bond or a linear or branched ($C_1$-$C_6$)alkylene chain,

M represents a single bond or a linear or branched ($C_1$-$C_6$)alkylene chain,

A and E each represents a nitrogen atom or a CH group, but at least one of the two groups A or E represents a nitrogen atom, W represents a group of formula (i) or (ii), and also may represent a group of formula (iii) but only when V represents a single bond and A represents a nitrogen atom, in which groups of formulae (i), (ii) and (iii):

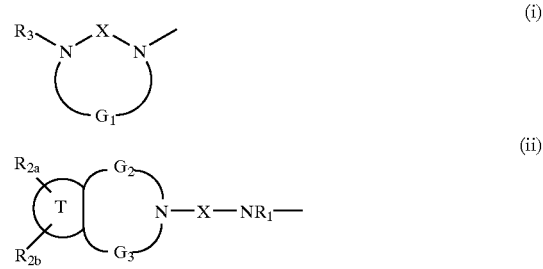

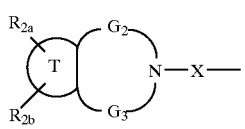
(iii)

X represents a carbonyl, sulphonyl or sulphoxide group, $G_1$ represents a linear $(C_2-C_4)$alkylene chain optionally containing a double bond and/or being optionally substituted by a hydroxyl group, $G_2$ represents a single bond or a methylene group, $G_3$ represents:
a linear $(C_2-C_3)$alkylene chain when $G_2$ represents a bond,
or a linear $(C_1-C_2)$alkylene chain when $G_2$ represents a methylene group,
the said alkylene chain in each of those cases optionally containing a double bond, T represents a phenyl group fused with the ring to which it is attached or a pyridyl group fused with the ring to which it is attached, $R_1$ represents a hydrogen atom, a linear or branched $(C_1-C_6)$alkyl group, an aryl group or an aryl-$(C_1-C_6)$ alkyl group in which the alkyl moiety is linear or branched, $R_{2a}$ and $R_{2b}$, which are the same or different, each independently of the other represents a group selected from a hydrogen atom, a halogen atom, a linear or branched $(C_1-C_6)$alkyl group, a hydroxy group, a linear or branched $(C_1-C_6)$alkoxy group, a mercapto group, a linear or branched $(C_1-C_6)$alkylthio group, a linear or branched $(C_1-C_6)$trihaloalkyl group, a cyano group, a nitro group, an amino group, a linear or branched $(C_1-C_6)$alkylamino group, a di-$(C_1-C_6)$alkylamino group in which each alkyl moiety may be linear or branched, a linear or branched $(C_1-C_6)$trihaloalkoxy group, an aryloxy group, an aryl-$(C_1-C_6)$alkoxy group in which the alkoxy moiety is linear or branched, a linear or branched $(C_1-C_6)$alkylsulphonate group, a linear or branched $(C_1-C_6)$trihaloalkylsulphonate group and a linear or branched $(C_1-C_6)$-alkylsulphonyl group, or $R_{2a}+R_{2b}$, taken together in adjacent positions, represent a group selected from methylenedioxy, 1,2-ethylenedioxy, 1,3-propylenedioxy, and ethylene optionally substituted by a group selected from cyano, hydroxymethyl, linear or branched $(C_1-C_6)$ alkoxycarbonyl, aryloxycarbonyl and aryl-$(C_1-C_6)$ alkoxycarbonyl in which the alkoxy moiety is linear or branched, $R_3$ represents an aryl or heteroaryl-A group, each of which groups may optionally be substituted by one or more groups, which may be the same or different, selected from among the definitions of $R_{2a}$, Y represents an aryloxy, heteroaryloxy or heteroaryl-B group, each of which groups may optionally be substituted by one or more groups, which may be the same or different, selected from among the definitions of $R_{2a}$, their isomers, their hydrates, their solvates and addition salts thereof with a pharmaceutically acceptable acid, wherein an aryl group is understood to mean a group selected from phenyl, biphenyl, naphthyl, dihydronaphthyl, tetrahydronaphthyl, indanyl, indenyl and benzocyclobutyl, a heteroaryl-A group is understood to mean a monocyclic aromatic or bicyclic, 5- to 12-membered system containing one or two hetero atoms, which may be the same or different, selected from oxygen, nitrogen and sulphur, and wherein, in the case of a bicyclic system, one of the rings has an aromatic character and the other ring may be aromatic or partially hydrogenated, a heteroaryl-B group is understood to mean a monocyclic aromatic or bicyclic aromatic, 5- to 12-membered system containing from 1 to 3 hetero atoms, which may be the same or different, selected from oxygen, nitrogen and sulphur, an aryloxy group is understood to mean an aryl group as defined hereinbefore attached to an oxygen atom, a heteroaryloxy group is understood to mean a heteroaryl-A group as defined hereinbefore attached to an oxygen atom, with the proviso that:
when V represents a single bond and W represents a group of formula (i) wherein $R_3$ represents a phenyl group, then Y cannot represent a 3-indolyl group,
when M represents a single bond and W represents a group of formula (i), then if Y represents a bicyclic heteroaryl-B group wherein one of the rings represents a benzene ring the said group Y cannot be joined to M by the said benzene ring,
and when M represents a single bond, V represents an ethylene group and W represents a group of formula (i) wherein $R_3$ represents a phenyl group, then Y cannot represent a 1,2-benzisoxazol-3-yl group.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid. malonic acid, succinic acid, glutaric acid, fumaric acid, tartaric acid, maleic acid, citric acid, ascorbic acid, oxalic acid, methanesulphonic acid, camphoric acid etc.

Preferred substituents Y according to the invention are the benzofuran-3-yl group and the phenyloxy group optionally substituted by a group $R_{2a}$ as defined for formula (I).

A preferred substituent X according to the invention is the carbonyl group.

According to an advantageous embodiment of the invention, preferred compounds are compounds of formula (I) wherein W represents a group of formula (I) as defined for formula (I).

Especially advantageously, preferred compounds of the invention are compounds of formula (IA):

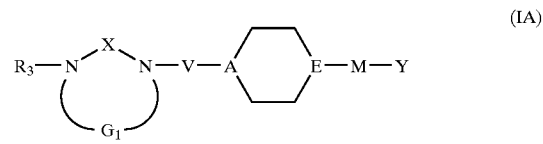
(IA)

wherein:
$R_3$ represents an aryl group, and advantageously a phenyl group, optionally substituted by a group selected from a halogen atom, a hydroxy group, a linear or branched $(C_1-C_6)$-alkoxy group, an aryl-$(C_1-C_6)$alkoxy group in which the alkoxy moiety is linear or branched, a nitro group, a linear or branched $(C_1-C_6)$trihaloalkyl group and a cyano group, X represents a carbonyl group, $G_1$ represents a linear $(C_2-C_3)$alkylene chain, V is as defined for formula (I), A represents a nitrogen atom when E represents a CH group, or A represents a CH group when E represents a nitrogen atom, M represents a linear or branched ($C_1$–$C_4$)alkylene chain, Y represents a benzofuran-3-yl group, or a phenyloxy group optionally substituted by a group selected from a halogen atom, a linear or branched ($C_1$–$C_6$) alkylsulphonyl group and a linear or branched ($C_1$–$C_6$) alkylthio group.

In a very preferable manner, preferred compounds of the invention are compounds of formula (IA) as defined hereinbefore wherein:

A represents a nitrogen atom and E represents a CH group when Y represents an optionally substituted phenyloxy group, or A represents a CH group and E represents a nitrogen atom when Y represents a benzofuran-3-yl group.

In another preferable manner, preferred compounds of the invention are compounds of formula (IA) as defined hereinbefore wherein V represents a single bond when Y represents a benzofuran-3-yl group and V represents a linear or branched ($C_1$–$C_4$)alkylene chain when Y represents an optionally substituted phenyloxy group.

According to another advantageous embodiment of the invention, preferred compounds are compounds of formula (I) wherein W represents a group of formula (ii) as defined for formula (I).

Especially advantageously, preferred compounds of the invention are compounds of formula (IB)

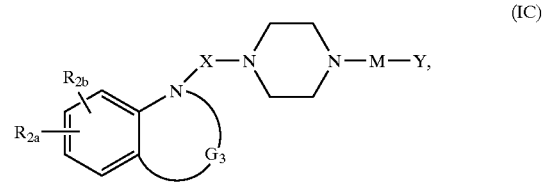

(IB)

wherein:

$R_{2a}$ and $R_{2b}$ are as defined for formula (I), $G_3$ represents a group of formula —$(CH_2)_2$—, —$(CH_2)_3$— or —CH=CH—, X represents a carbonyl group, $R_1$ represents a hydrogen atom, A, E and V are as defined for formula (I), M represents a linear or branched ($C_1$–$C_4$)alkylene chain, Y represents a benzofuran-3-yl group, or a phenyloxy group optionally substituted by a group selected from a halogen atom, a linear or branched ($C_1$–$C_6$) alkylsulphonyl group and a linear or branched ($C_1$–$C_6$) alkylthio group.

In a very preferable manner, preferred compounds of the invention are compounds of formula (IB) as defined hereinbefore wherein:

A represents a nitrogen atom and E represents a CH group when Y represents an optionally substituted phenyloxy group, or A represents a CH group and E represents a nitrogen atom when Y represents a benzofuran-3-yl group.

In another preferable manner, preferred compounds of the invention are compounds of formula (IB) as defined hereinbefore wherein V represents a single bond when Y represents a benzofuran-3-yl group and V represents a linear or branched ($C_1$–$C_4$)alkylene chain when Y represents an optionally substituted phenyloxy group.

According to a third advantageous embodiment of the invention, preferred compounds are compounds of formula (I) wherein W represents a group of formula (iii) as defined for formula (I).

Especially advantageously, preferred compounds of the invention are compounds of formula (IC):

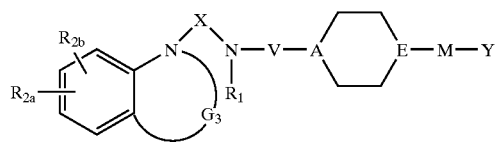

(IC)

wherein:

$R_{2a}$, $R_{2b}$ and M are as defined for formula (I), $G_3$ represents a group of formula —$(CH_2)_2$—, X represents a carbonyl group, Y represents a benzofuran-3-yl group, or a phenyloxy group optionally substituted by a group selected from a halogen atom and a linear or branched ($C_1$–$C_6$) alkylsulphonyl group.

Preferred compounds of the invention are:

N-{2-[4-(phenoxymethyl)-1-piperidyl]ethyl}-1-indolinecarboxamide, 5-fluoro-N-(2-{4-[2-(4-fluorophenoxy)ethyl]-1-piperidyl}ethyl)-1-indolinecarboxamide, N-{2-[4-(p-fluorophenoxymethyl)-1-piperidyl]ethyl}-1-indolinecarboxamide, N-{2-[4-(phenoxymethyl)-1-piperidyl]ethyl}-1-indolecarboxamide, and 1-(2-{4-[2-(4-fluorophenoxy)ethyl]-1-piperidyl}ethyl)-3-phenyl-2-imidazolidinone.

The isomers, as well as the hydrates, solvates and addition salts with a pharmaceutically acceptable acid, of the preferred compounds form an integral part of the invention.

The invention relates also to a process for the preparation of compounds of formula (I), which process is characterised in that there is used as starting material:

a compound of formula (II):

$R_3$—N=C=O     (II), wherein $R_3$ is as defined for formula (I),
which is reacted
with a compound of formula (III):

HO-$G_{1a}$-NH—$V_a$—OH     (III), wherein $V_a$ represents a ($C_2$–$C_6$)alkylene chain and $G_{1a}$ represents a linear ($C_2$–$C_3$)alkylene chain,
to yield the compounds of formula (IVa):

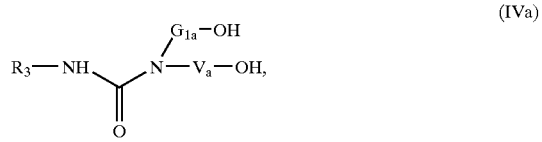

(IVa)

wherein $R_3$, $G_{1a}$ and $V_a$ are as defined hereinbefore, which compounds of formula (IVa) are converted by conventional methods of organic synthesis to yield the compounds of formula (IVb):

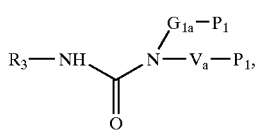
(IVb)

wherein $P_1$ represents a chlorine, bromine or iodine atom or a group $OSO_2R_4$ wherein $R_4$ represents a methyl, trifluoromethyl or tolyl group, and $R_3$, $V_a$ and $G_{1a}$ are as defined hereinbefore,
which compounds of formula (IVb) are subjected to the action of heat
to yield the compounds of formula (IVc):

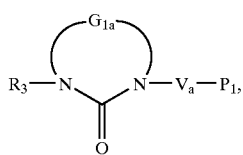
(IVc)

wherein $R_3$, $G_{1a}$, $V_a$ and $P_1$ are as defined hereinbefore, which compounds of formula (IVc) are treated under basic conditions with a compound of formula (V):

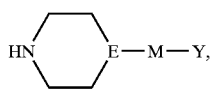
(V)

wherein E, M and Y are as defined for formula (I),
to yield the compounds of formula (I/a), a particular case of the compounds of formula (I):

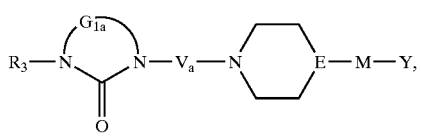
(I/a)

wherein $R_3$, $G_{1a}$, $V_a$, E, M and Y are as defined hereinbefore, or with a compound of formula (VI):

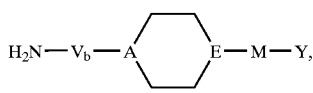
(VI)

wherein A, E, M and Y have the same meanings as in formula (I) and $V_b$ represents a $(C_1-C_6)$alkylene chain,
to yield the compounds of formula (VII):

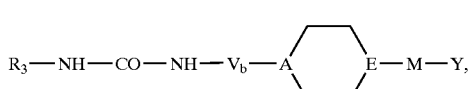
(VII)

wherein $R_3$, $V_b$, A, E, M and Y are as defined hereinbefore, which compounds of formula (VII) are treated in the presence of a strong base with a compound of formula (VIII):

$P_1$-$G_{1b}$-$P'_1$ (VIII), wherein $P_1$ and $P'_1$, which are the same or different, are as defined for $P_1$ hereinbefore and $G_{1b}$ represents a $C_4$alkylene chain optionally containing a double bond,
to yield the compounds of formula (I/b), a particular case of the compounds of formula (I):

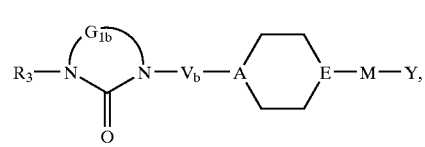
(I/b)

wherein $R_3$, $G_{1b}$, $V_b$, A, E, M and Y are as defined hereinbefore,
or with a compound of formula (IX):

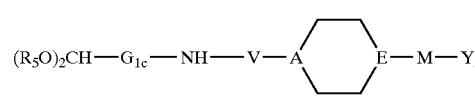
(IX)

wherein $G_{1c}$ represents a linear $C_1$- or $C_2$-alkylene chain, $R_5$ represents a linear or branched $(C_1-C_6)$alkyl group, and V, A, E, M and Y are as defined for formula (I),
to yield the compounds of formula (X):

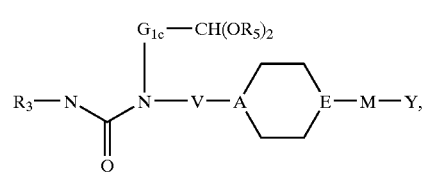
(X)

wherein $R_3$, $G_{1c}$, V, A, $R_5$, M and Y are as defined hereinbefore, which compounds of formula (X) are placed in the presence of a strong organic acid
to yield the compounds of formula (I/c), a particular case of the compounds of formula (I):

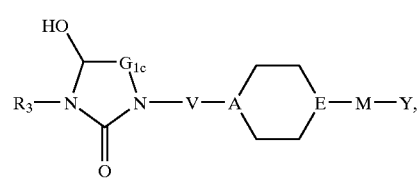
(I/c)

wherein $R_3$, $G_{1c}$, V, A, E, M and Y are as defined hereinbefore, which compound of formula (I/c) is hydrogenated according to conventional techniques of organic synthesis
to yield the compounds of formula (I/d), a particular case of the compounds of formula (I):

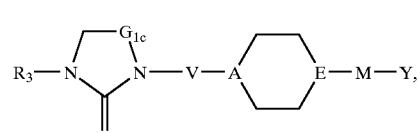
(I/d)

wherein $R_3$, $G_{1c}$, V, A, E, M and Y are as defined hereinbefore, or which compounds of formula (I/c) are dehydrated under conventional conditions of organic synthesis to yield the compounds of formula (I/e), a particular case of the compounds of formula (I):

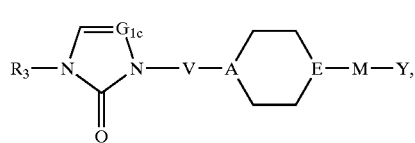
(I/e)

wherein $R_3$, $G_{1c}$, V, A, E, M and Y are as defined hereinbefore, or a compound of formula (IIa):

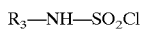
(IIa), wherein $R_3$ is as defined for formula (I), which is reacted with a compound of formula (IIIa):

(IIIa), wherein Hal represents a halogen atom and $G_{1a}$ and $V_a$ have the same meanings as hereinbefore,
to yield the compounds of formula (IIIb):

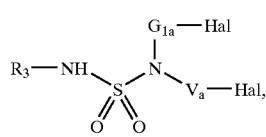
(IIIb)

wherein $R_3$, $G_{1a}$, $V_a$ and Hal are as defined hereinbefore, which compounds of formula (IIIb) are reacted to yield the compounds of formula (IIIc):

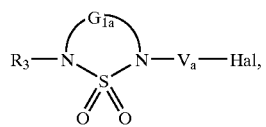
(IIIc)

wherein $R_3$, $G_{1a}$, $V_a$ and Hal are as defined hereinbefore, which compounds of formula (IIIc) are treated under basic conditions with a compound of formula (V):

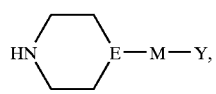
(V)

wherein E, M and Y are as defined for formula (I),
to yield the compounds of formula (I/i), a particular case of the compounds of formula (I):

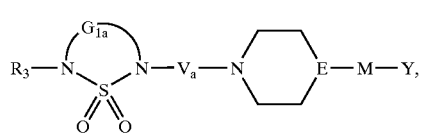
(I/i)

wherein $R_3$, $G_{1a}$, $V_a$, E, M and Y are as defined hereinbefore, or a compound of formula (XV):

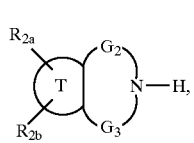
(XV)

wherein $R_{2a}$, $R_{2b}$, $G_2$, $G_3$ and T have the same meanings as in formula (I), which compound of formula (XV) is treated either with diphosgene or triphosgene, in the presence of a base, or with di-(1H-imidazol-1-yl)methanone to yield the compounds of formula (XVI):

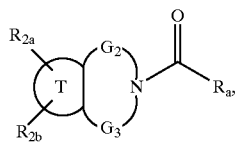
(XVI)

wherein $R_{2a}$, $R_{2b}$, $G_2$, $G_3$ and T are as defined hereinbefore and $R_a$ represents a chlorine atom, a 1H-imidazol-1-yl group or
a group of formula:

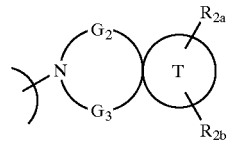

wherein $R_{2a}$, $R_{2b}$, $G_2$, $G_3$ and T are as defined hereinbefore, which compound of formula (XVI) is reacted with a compound of formula (XVII):

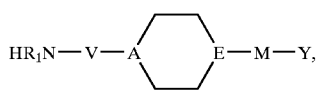
(XVII)

wherein $R_1$, V, A, E, M and Y are as defined for formula (I), to yield the compounds of formula (I/f), a particular case of the compounds of formula (I):

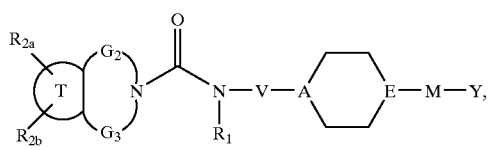
(I/f)

wherein $R_{2a}$, $R_{2b}$, $G_2$, $G_3$, T, $R_1$, V, A, E, M and Y are as defined for formula (I), or which compound of formula (XV) is treated under basic conditions with diphosgene, with triphosgene, with $SO_2Cl_2$, with $SOCl_2$, with di-(1H-imidazol-1-yl) methanone or with di-(1H-imidazol-1-yl)sulphonyl, to yield the compounds of formula (XVIII):

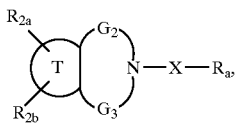
(XVIII)

wherein $R_{2a}$, $R_{2b}$, $G_2$, $G_3$, T and X have the same meanings as in formula (I) and $R_a$ is as defined hereinbefore, which compounds of formula (XVIII) are placed in the presence of a compound of formula (V) as described hereinbefore to yield the compounds of formula (I/g), a particular case of the compounds of formula (I):

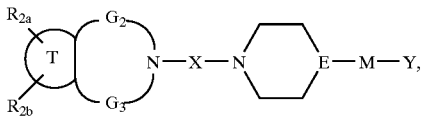
(I/g)

wherein $R_{2a}$, $R_{2b}$, $G_2$, $G_3$, T, X, E, M and Y are as defined hereinbefore, or finally which compound of formula (XV) is reacted with chlorosulphonyl isocyanate, in the presence of a compound of formula (XIX):

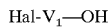

Hal-$V_1$—OH  (XIX), wherein $V_1$ represents a linear ($C_2$-$C_6$)alkylene chain and Hal represents a chlorine, bromine or iodine atom, to yield the compounds of formula (XX):

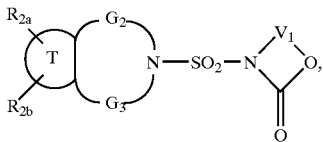
(XX)

wherein $R_{2a}$, $R_{2b}$, $G_2$, $G_3$, T and $V_1$ are as defined hereinbefore, which compound of formula (XX) is then treated in succession with an alkali metal hydroxide and then with carbon tetrabromide in the presence of triphenylphosphine to yield the compounds of formula (XXI):

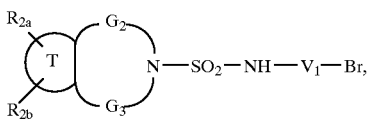
(XXI)

wherein $R_{2a}$, $R_{2b}$, $G_2$, $G_3$, T and $V_1$ are as defined hereinbefore, which compounds of formula (XXI) are reacted with a compound of formula (V) as described hereinbefore, to yield the compounds of formula (I/h), a particular case of the compounds of formula (I):

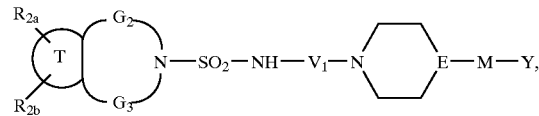
(I/h)

wherein $R_{2a}$, $R_{2b}$, $G_2$, $G_3$, T, $V_1$, E, M and Y are as defined hereinbefore, the totality of the compounds of formulae (I/a) to (I/i) constituting the compounds of the invention, which are purified, if necessary, according to conventional purification techniques, are separated, where appropriate, into their isomers according to a conventional separation technique and are converted, if desired, into their hydrates, solvates or addition salts with a pharmaceutically acceptable acid.

The compounds of formulae (II), (III), (V), (VI), (VIII), (IX), (XV), (XVII) and (XIX) are either commercial products or are obtained according to known and conventional methods of organic synthesis.

The compounds of the present invention are useful in the treatment of diseases or pathological conditions in which endothelial dysfunction is known. Accordingly, by virtue of their specific pharmacological activity, the compounds of the invention are useful in preventing the development, extension and complications of atherosclerotic lesions, in particular for patients having a vascular risk factor (dyslipidaemia, diabetes, systemic arterial hypertension), in the treatment of myocardial or peripheral ischaemia, of cardiac insufficiency and of pulmonary arterial hypertension and in the prevention of vascular complications after vascular bypass, vascular dilatation, repermeabilisation and heart transplantation.

The present invention relates also to pharmaceutical compositions comprising as active ingredient at least one compound of formula (I), an optical isomer, hydrate, solvate or addition salt thereof with a pharmaceutically acceptable acid, alone or in combination with one or more inert, non-toxic, pharmaceutically acceptable excipients or carriers.

Among the pharmaceutical compositions according to the invention there may be mentioned more especially those that are suitable for oral, parenteral (intravenous, intramuscular or sub-cutaneous), per- or trans-cutaneous, nasal, rectal, perlingual, ocular or respiratory administration, and especially tablets or dragées, sublingual tablets, soft gelatin capsules, hard gelatin capsules, suppositories, creams, ointments, dermal gels, injectable or drinkable preparations, aerosols, eye or nose drops etc. . . .

The useful dosage varies according to the age and weight of the patient, the route of administration, the nature and severity of the disorder and any associated treatments taken, and ranges from 1 mg to 200 mg in one or more administrations per day.

The following Examples illustrate the invention but do not limit it in any way. The starting materials used are known products or are prepared according to known procedures. The different Preparations yield synthesis intermediates that are useful in preparation of the compounds of the invention.

The structures of the compounds described in the Examples were determined according to the usual spectrophotometric techniques (infrared, nuclear magnetic resonance, mass spectrometry, . . . ).

The melting points were determined using either a Kofler hot-plate (K.) or a hot-plate under a microscope (M.K.).

Preparation 1

4-(p-Fluorophenoxymethyl)piperidine

Step 1: N-tert-butyloxycarbonyl4-(p-fluorophenoxymethyl) piperidine

Over the course of 30 minutes, 10.5 ml of diethyl azodicarboxylate are poured onto a mixture of 13.5 g of N-tert-butyloxycarbonyl-4-hydroxymethylpiperidine, 7.45 g of p-fluorophenol, 17.4 g of triphenylphosphine and 140 ml of tetrahydrofuran. After stirring for 12 hours at ambient temperature, the reaction mixture is concentrated, taken up in ether, washed with water and then 1N sodium hydroxide solution, and then washed with water. After drying, filtration and evaporation under reduced pressure, chromatography over silica gel (cyclohexane/ethyl acetate: 90/10) allows the expected product to be isolated.

Melting point (K): 94–98° C.

Step 2: 4-(p-Fluorophenoxymethyl)piperidine 12.1 g of the product obtained in Step 1 are treated, at ambient temperature, with 300 ml of ethereal hydrogen chloride solution for 48 hours, allowing the title product to be obtained in the form of the hydrochloride. The free base is obtained by treating the hydrochloride with 1N sodium hydroxide solution followed by extraction with dichloromethane.

Preparation 2

4-[2-(p-Fluorophenoxy)ethyl]piperidine

The product is obtained according to the procedure of Preparation 1 using 2-(N-tert-butyloxycarbonyl-4-piperidyl)ethanol as substrate in Step 1.

Preparation 3

4-(Phenoxymethyl)piperidine

The product is obtained according to the procedure of Preparation 1 using phenol instead of p-fluorophenol in Step 1.

Preparation 4

4-(p-Methylsulphonylphenoxymethyl)piperidine

The product is obtained according to the procedure of Preparation 1 using p-methyl-sulphonylphenol instead of p-fluorophenol in Step 1.

Melting point (hydrochloride): 230–234° C.

Preparation 5

4-[2-(p-Methylsulphonylphenoxy)ethyl]piperidine

The product is obtained according to the procedure of Preparation 1 using 2-(N-tert-butyloxycarbonyl-4-piperidyl)ethanol and p-methylsulphonylphenol in Step 1.

Preparation 6

2-{4-[(4-Methylsulphonylphenoxy)methyl]-1-piperidyl}-ethylamine

Step 1: 1-tert-Butyloxycarbonyl-2-{4-[(4-methylsulphonylphenoxy)methyl]-1-piperidyl}ethylamine 11.1 mmol of the product of Preparation 4, 11.1 mmol of 1-tert-butyloxycarbonyl-2-bromoethylamine, 4.6 g of sodium carbonate and a spatula tip of potassium iodide are added to 50 ml of methyl isobutyl ketone. After 8 hours at reflux and then 12 hours at ambient temperature, a white solid is obtained which is recrystallised from acetonitrile, allowing the expected product to be isolated.

Step 2: 2-{4-[(4-Methylsulphonylphenoxy)methyl]-1-piperidyl}ethylamine

The procedure is as in Step 2 of Preparation 1.

Preparation 7

1-[2-(Benzofuran-3-yl)ethyl]-4-piperidylamine

Step 1: N-tert-butyloxycarbonyl-1-[2-(benzofuran-3-yl)ethyl]-4-piperidylamine 10 mmol of 2-(benzofuran-3-yl)-1-bromoethane, 9.62 mmol of tert-butyl 4-piperidyl-carbamate, 2.65 g of potassium carbonate and 0.65 g of tetrabutylammonium sulphate are added to 10 ml of toluene. After refluxing for 12 hours, the mixture is taken up in water. The organic phase is then washed with water, dried and then filtered. Evaporation under reduced pressure allows the expected product to be isolated.

Step 2: 1-[2-(Benzofuran-3-yl)ethyl]-4-piperidylamine

The procedure is as in Step 2 of Preparation 1.

Preparation 8

1-[3-(Benzofuran-3-yl)propyl]-4-piperidylamine

The product is obtained according to the procedure of Preparation 7 using 3-(benzofuran-3-yl)-1-bromopropane as substrate in Step 1.

Preparation 9

N-{1-[2-(benzofuran-3-yl)ethyl]-4-piperidyl}-N-(2, 2-dimethoxyethyl)amine 12.3 mmol of the product of Preparation 7 and 12.3 mmol of glyoxal 1,1-dimethyl acetal as a 45% solution in tert-butyl methyl ether are added to 50 ml of dichloromethane. After reacting for 15 minutes, 18.45 mmol of sodium triacetoxyborohydride and then 0.69 ml of acetic acid are added. After 12 hours, the reaction mixture is poured onto 100 ml of 1N sodium hydroxide solution. The organic phase is then washed with water, dried and then filtered. Evaporation under reduced pressure allows the expected product to be obtained.

Preparation 10

N-({1-[3-(benzofuran-3-yl)propyl]-4-piperidyl)-N-(2,2-dimethoxyethyl)amine

The product is obtained according to the procedure of Preparation 9 using the product of Preparation 8 instead of that of Preparation 7 as substrate.

Preparation 11

N-{1-[2-(benzofuran-3-yl)ethyl]-4-piperidyl}-N-(3, 3-diethoxypropyl)amine

The product is obtained according to the procedure of Preparation 9 using, as substrate, the product of Preparation 7 and 3-amino-propionaldehyde diethyl acetal.

Preparation 12

N-{1-[3-(benzofuran-3-yl)propyl]-4-piperidyl}-N-(3, 3-diethoxypropyl)amine

The product is obtained according to the procedure of Preparation 9 using, as substrate, the product of Preparation 8 and 3-amino-propionaldehyde diethyl acetal.

Preparation 13

1-[2-(Benzofuran-3-yl)ethyl]piperazine 84 mmol of 2-(benzofuran-3-yl)-1-bromoethane, 67 mmol of piperazine and 56 mmol of potassium carbonate are added to 200 ml of acetonitrile. After refluxing for 4 hours, the reaction mixture is cooled and then concentrated. The residue is taken up in dichloromethane, is washed with water, dried, filtered and then concentrated under reduced pressure. Chromatography over silica gel (dichloromethane/ethanol: 90/10) allows the expected product to be isolated.

Preparation 14

1-[3-(Benzofuran-3-yl)propyl]piperazine

The product is obtained according to the procedure of Preparation 13 using 3-(benzofuran-3-yl)-1-bromopropane as substrate.

Preparation 15

1-[2-(p-Fluorophenoxy)ethyl]piperazine

The product is obtained according to the procedure of Preparation 13 using 1-bromo-2-(p-fluorophenoxy)ethane as substrate.

Preparation 16

1-[3-(p-Fluorophenoxy)propyl]piperazine

The product is obtained according to the procedure of Preparation 13 using 1-bromo-3-(p-fluorophenoxy)propane as substrate.

Preparation 17

2-{4-[2-(p-Fluorophenoxy)ethyl]-1-piperidyl}ethylamine

Step 1: {4-[2-(Fluorophenoxy)ethyl]-1-piperidyl}acetonitrile 92.4 mmol of the product of Preparation 2, 6.5 ml of bromoacetonitrile and 39.2 g of potassium carbonate are added to 320 ml of methyl isobutyl ketone. After refluxing for 12 hours, the reaction mixture is filtered and concentrated under reduced pressure. The residue is taken up in water and dichloromethane. The organic phase is washed with water, dried, filtered and then concentrated under reduced pressure, allowing the expected product to be obtained.

Melting point (K): 72° C.

Step 2: 2-{4-[2-(p-Fluorophenoxy)ethyl]-1-piperidyl}ethylamine

A solution of the product obtained in Step 1 dissolved in 200 ml of tetrahydrofuran is added to a suspension of 81 mmol of LiAlH$_4$ in 200 ml of tetrahydrofuran, maintained at 0° C. After stirring for 12 hours at ambient temperature, the reaction mixture is hydrolysed using 2.75 ml of water, 2.2 ml of 20% sodium hydroxide solution and then 10 ml of water. After filtration and rinsing with tetrahydrofuran, the filtrate is dried and then concentrated under reduced pressure, allowing the expected product to be isolated.

Preparation 18

2-[4-(p-Fluorophenoxymethyl)-1-piperidyl]ethylamine

The product is obtained according to the procedure of Preparation 17 using the product of Preparation 1 as substrate.

Preparation 19

2-[4-(Phenoxymethyl)-1-piperidyl]ethylamine

The product is obtained according to the procedure of Preparation 17 using the product of Preparation 3 as substrate.

Preparation 20

2-{4-[2-(Phenoxy)ethyl]-1-piperidyl}ethylamine

The product is obtained according to the procedure of Preparation 17 using 4-(2-phenoxy-ethyl)piperidine as substrate.

Preparation 21

{1-[3-(p-Fluorophenoxy)propyl]-4-piperidyl}methylamine

The product is obtained according to the procedure described in Step 2 of Preparation 17 using {1-[3-(p-fluorophenoxy)propyl]-4-piperidyl}formamide as substrate and maintaining the reaction for 3 hours at reflux and then for 12 hours at ambient temperature.

Preparation 22

1-[2-(p-Fluorophenoxy)ethyl]4-piperidylamine

The product is obtained according to the procedure of Preparation 7 using 1-bromo-2-(p-fluorophenoxy)ethane as substrate.

Preparation 23

1-(2-Chloroethyl)-3-phenyl-2-imidazolidinone

Step 1: 1,1-Bis(2-hydroxyethyl)-3-phenylurea 0.163 mol of diethanolamine dissolved in 160 ml of dichloromethane is added, at 10° C., to a solution of 0.168 mol of phenyl isocyanate. After reacting for 1 hour at 10° C. and then for 12 hours at ambient temperature, the reaction mixture is concentrated under reduced pressure.

Step 2: 1,1-Bis(2-chloroethyl)-3-phenylurea 26.44 ml of thionyl chloride are added, at 0° C., to a solution of 0.173 mol of the product obtained in Step 1 in 100 ml of dichloromethane. After reacting for 4 hours at reflux and then for 12 hours at ambient temperature, the reaction mixture is concentrated under reduced pressure.

Step 3: 1-(2-Chloroethyl)-3-phenyl-2-imidazolidinone 0.167 mol of the product obtained in Step 2 is heated for 3 hours at 120° C. and then for 6 hours at 140° C. When no more gas is evolved, cooling is carried out. Chromatography over silica gel (dichloromethane) allows the expected product to be isolated.

Melting point (K): 92° C.

Preparation 24

1-(2-Chloroethyl)-3-(p-methoxyphenyl)-2-imidazolidinone

The product is obtained according to the procedure of Preparation 23 using p-methoxy-phenyl isocyanate in Step 1.

Melting point (K): 118° C.

Preparation 25

1-(2-Chloroethyl)-3-(p-hydroxyethyl)-2-imidazolidinone

The product is obtained during purification of Preparation 24 over silica gel and is isolated in a ratio of 1:2.

Melting point (K): 171° C.

Preparation 26

1-(2-Chloroethyl)-3-(o-chlorophenyl)-2-imidazolidinone

The product is obtained according to the procedure of Preparation 23 using o-chlorophenyl isocyanate in Step 1.

Preparation 27

1-(2-Chloroethyl)-3-(p-fluorophenyl)-2-imidazolidinone

The product is obtained according to the procedure of Preparation 23 using p-fluorophenyl isocyanate in Step 1.

Melting point (K): 105° C.

Preparation 28

3-(p-Benzyloxyphenyl)-1-(2-chloroethyl)-2-imidazolidinone

The product is obtained according to the procedure of Preparation 23 using p-benzyloxyphenyl isocyanate in Step 1.

Melting point (M.K.): 128–133° C.

Preparation 29

1-(2-Chloroethyl)-3-(p-nitrophenyl)-2-imidazolidinone

The product is obtained according to the procedure of Preparation 23 using p-nitrophenyl isocyanate in Step 1.

Melting point (M.K.): 134° C.

Preparation 30

1-(2-Chloroethyl)-3-(p-chlorophenyl)-2-imidazolidinone

The product is obtained according to the procedure of Preparation 23 using p-chlorophenyl isocyanate in Step 1.

Melting point (M.K.): 112–114° C.

Preparation 31

4-[2-p-Chlorophenoxy)ethyl]piperidine

The product is obtained according to the procedure of Preparation 1, Steps 1 and 2, using 2-(N-tert-butyloxycarbonyl-4-piperidyl)ethanol and p-chlorophenol as substrates.

Melting point of the hydrochloride (K.): 205° C.

Preparation 32

4-[(p-Methylthiophenoxy)methyl]piperidine

The product is obtained according to the procedure of Preparation 1, Steps 1 and 2, using p-methylthiophenol as substrate.

Melting point of the hydrochloride (M.K.): 206–210° C.

Preparation 33

4-[2-(p-Methylthiophenoxy)ethyl]piperidine

The product is obtained according to the procedure of Preparation 1, Steps 1 and 2, using, as substrates, that of Preparation 2 and that of Preparation 32.

Melting point of the hydrochloride (M.K.): 146–150° C.

Preparation 34

4-[2-(Phenoxy)ethyl]piperidine

The product is obtained according to the procedure of Preparation 1, Steps 1 and 2, using 2-(N-tert-butyloxycarbonyl4-piperidyl)ethanol and phenol as substrates.

Melting point of the hydrochloride (K.): 155° C.

Preparation 35

1-(2-Chloroethyl)-3-(p-trifluoromethylphenyl) -2-imidazolidinone

The product is obtained according to the procedure of Preparation 23, Steps 1 to 3, using p-trifluoromethylphenyl isocyanate as substrate in Step 1.

Melting point (K.): 70° C.

Preparation 36

1-(2-Chloroethyl)-3-(p-cyanophenyl)-2-imidazolidinone

The product is obtained according to the procedure of Preparation 23, Steps 1 to 3, using p-cyanophenyl isocyanate as substrate in Step 1.

Melting point (K.): 149° C.

Preparation 37

N-(2,2-Dimethoxyethyl)-N-(2-{4-[2-(4-fluorophenoxy)ethyl]-1-piperidyl}ethyl)amine The product is obtained in the form of an oil according to the procedure of Preparation 9 using the product of Preparation 17 as substrate.

Preparation 38

2-(2-Chloroethyl)-5-phenyl-1,2,5-thiadiazolidine-1,1-dioxide

Step 1: Phenylsulphamoyl Chloride 25.2 g of chlorosulphonic acid are added slowly to a solution of 60.6 g of aniline in 316 ml of methylene chloride cooled to −5° C. When the addition is complete, the mixture is allowed to return to ambient temperature and the precipitate obtained is filtered off. After drying, the precipitate is taken up in 231 ml of toluene, and 45.1 g of phosphorus pentachloride are added gradually. The mixture is then refluxed for 3 hours 30 minutes and, after returning to ambient temperature, the precipitate formed is filtered off. The filtrate is concentrated to obtain the expected product.

Step 2: N,N-bis(2chloroethyl)-N'-phenylsulphamide 66 g of the product obtained in Step 1 above are added to a suspension of 38.6 g of N,N-bis(2-chloroethyl)amine hydrochloride in 265 ml of xylene heated to 100° C. The reaction mixture is heated at 140° C. for 12 hours and, after cooling, filtered over a frit. The filtrate is concentrated and then purified by flash chromatography (eluant $CH_2Cl_2$/AcOEt: 95/5) to yield the expected product.

Step 3: 2-(2-Chloroethyl)-5-phenyl-1,2,5-thiadiazolidine-1,1-dioxide

Using a slow dropper, a solution of 12.6 g of the product obtained in Step 2 above in 25 ml of DMF is introduced onto a suspension of 1.4 g of NaH in 175 ml of DMF and stirring is carried out for 12 hours. The reaction mixture is then poured onto ice in order to bring about crystallisation of the expected product.

Melting point (K.): 45° C.

Preparation 39

2-(2-Chloroethyl)-5-(4-chlorophenyl)-1,2,5-thiadiazolidine-1,1-dioxide

The product is obtained according to the procedure of Preparation 38 using p-chloroaniline as substrate in Step 1.

Melting point (K.): 90° C.

Preparation 40

2-(2-Chloroethyl)-5-(4-fluorophenyl)-1,2,5-thiadiazolidine-1,1-dioxide

The product is obtained according to the procedure of Preparation 38 using p-fluoroaniline as substrate in Step 1.

Melting point (K.): 65° C.

Preparation 41

2-[4-(p-Methylthiophenoxymethyl)-1-piperidyl] ethylamine

The product is obtained according to the procedure of Preparation 17 using, as substrate, 4-(p-methylthiophenoxymethyl)piperidine, which is obtained according to the procedure of Preparation 1 using, in Step 1, p-(methylthio)-phenol instead of p-fluorophenol.

Melting point (K.): 60–66° C.

Preparation 42

N-Methyl-2-[4-(phenoxymethyl)-1-piperidyl] ethanamine 5 g of di-tert-butyl dicarbonate are introduced into a solution of 5 g of the product of Preparation 19 in 40 ml of methylene chloride and the mixture is stirred for 24 hours. After concentration in vacuo, the reaction mixture is purified by flash chromatography (eluant: $CH_2Cl_2$/EtOH: 95/5). The product obtained (5.5 g) is dissolved in 50 ml of THF and poured onto a suspension of 1.7 g lithium aluminium hydride in 70 ml of THF. The reaction mixture is refluxed for 7 hours and then, after cooling, hydrolysed at 5° C. with, in succession, 11.7 ml of $H_2O$, 6.1 ml of 20% sodium hydroxide solution and a further 6.7 ml of water. After filtration and concentration, the expected product is obtained.

Preparation 43

2-{4-[2-(1-Benzofuran-3-yl)ethyl]-1-piperazinyl}ethanamine

The product is obtained in the form of an oil according to the procedure of Preparation 17 using the product of Preparation 13 as substrate in Step 1.

Preparation 44

2-{4-[2-(4-Fluorophenoxy)ethyl]-1-piperazinyl}ethanamine

The product is obtained in the form of a colourless oil according to the procedure of Preparation 17 using the product of Preparation 15 as substrate in Step 1.

Preparation 45

5-Methoxy-1H-pyrrolo[2,3-c]pyridine

Step 1: 2-Methoxy-4-methyl-5-nitropyridine 22.3 g of 2-hydroxy-4-methyl-5-nitropyridine and 170 ml of $POCl_3$ are mixed together and heated at 100° C. for 3 hours. The cooled reaction medium is poured onto ice to yield a beige precipitate of 2-chloro-4-methyl-5-nitropyridine.

Melting point (M.K.): 38–39° C.

10.95 g of sodium methanolate are added, in portions, to 5 g of the resulting precipitate dissolved in 110 ml of methanol. The reaction is exothermic and, when the addition is complete, the mixture is refluxed for 2 hours. After returning to ambient temperature, the reaction mixture is poured onto a mixture of 200 g of ice and 100 ml of water. The precipitate obtained corresponds to the expected product.

Melting point (M.K.): 80–84° C.

Step 2: 5-Methoxy-1H-pyrrolo[2,3-c]pyridine 10.76 g of N,N-dimethylformamide dimethyl acetal and 2.45 ml of pyrrolidine are added, in succession, to a solution of 5 g of the product obtained in Step 1 in 60 ml of dimethylformamide. The mixture obtained is first heated at 100° C. for 8 hours and then at 150° C. for 1 hour. Concentration is carried out under a vacuum of $10^{-1}$ mbar and the residue is taken up in 150 ml of tetrahydrofuran. The solution obtained is hydrogenated under a pressure of 10 bars for 4 hours in the presence of 10% Pd/C. After filtration and concentration, the residue is chromatographed over silica (eluant $CH_2Cl_2$/EtOH: 95/5) to yield the expected product.

Melting point (M.K.): 126–130° C.

EXAMPLE 1

1-{1-[2-(Benzofuran-3-yl)ethyl]-4-piperidyl}-3-phenyl-1,3-dihydro-2H-imidazol-2-one and its Hydrochloride Step 1: 1-{1-[2-(Benzofuran-3-yl)ethyl]-4-piperidyl}-1-(2,2-dimethoxyethyl)-3-phenylurea 6 mmol of phenyl isocyanate are added to a mixture of 6 mmol of the compound of Preparation 9 and 3.14 ml of diisopropylethylamine in 72 ml of dichloromethane. After stirring for 12 hours at ambient temperature and dilution with water, the organic phase is washed with water, dried, filtered and then concentrated under reduced pressure, allowing the expected product to be obtained.

Step 2: 1-{1-[2-(Benzofuran-3-yl)ethyl]-4-piperidyl}-3-phenyl-1,3-dihydro-2H-imidazol-2-one and its Hydrochloride 67 mmol of the compound obtained in Step 1 are placed in the presence of 20.7 ml of trifluoroacetic acid, 20 ml of water and 132 ml of dichloromethane. After stirring for 12 hours at ambient temperature, the reaction mixture is neutralised using sodium hydroxide; the organic phase is then washed with water, dried, filtered and then evaporated. Chromatography over silica gel allows a product to be isolated, the instantaneous melting point of which is 154° C.

The product is converted into its hydrochloride after being dissolved in dichloromethane. It is recrystallised from ethanol.

| Melting point (M.K.): 220–225° C. Elemental microanalysis: | | | | |
|---|---|---|---|---|
| | C | H | N | Cl |
| % found | 68.15 | 6.28 | 9.86 | 8.36 |
| % calculated | 68.00 | 6.18 | 9.91 | 8.36 |

EXAMPLE 2

1-{1-[3-(Benzofuran-3-yl)propyl]-4-piperidyl}-3-phenyl-1,3-dihydro-2H-imidazol-2-one and its Hydrochloride The product is obtained as in Example 1 using the compound of Preparation 10 as substrate in Step 1. Its hydrochloride, prepared starting from ethanolic hydrogen chloride solution, is recrystallised from isopropanol.

| Melting point (M.K.): 210–214° C. Elemental microanalysis: | | | | |
|---|---|---|---|---|
| | C | H | N | Cl |
| % found | 68.30 | 6.36 | 9.48 | 8.35 |
| % calculated | 68.56 | 6.44 | 9.59 | 8.09 |

EXAMPLE 3

1-{1-[3-(Benzofuran-3-yl)propyl]-4-piperidyl}-3-phenyl-2-imidazolidinone and its Hydrochloride 3.17 mmol of the compound of Example 2 are hydrogenated in acetic acid in the presence of 10% Pd/C at ambient temperature and atmospheric pressure. When the reaction is complete, the catalyst is filtered off and the filtrate is concentrated, taken up in ethyl acetate and sodium hydroxide solution, washed with water, dried and evaporated. The product obtained is converted into its hydrochloride using ethanolic hydrogen chloride.

| Melting point (M.K.): 235–240° C. Elemental microanalysis: | | | | |
|---|---|---|---|---|
| | C | H | N | Cl |
| % found | 68.15 | 6.80 | 9.29 | 8.18 |
| % calculated | 68.25 | 6.87 | 9.55 | 8.06 |

EXAMPLE 4

1-{1-[2-(Benzofuran-3-yl)ethyl]-4-piperidyl}-3-phenyl-2-imidazolidinone and its Hydrochloride The product is obtained according to the procedure of Example 3 using the compound of Example 1 as substrate.

| Melting point (M.K.): 224–228° C. Elemental microanalysis: | | | | |
|---|---|---|---|---|
| | C | H | N | Cl |
| % found | 66.99 | 6.51 | 9.75 | 8.45 |
| % calculated | 67.67 | 6.63 | 9.86 | 8.32 |

EXAMPLE 5

1-(2-{4-[2-(p-Fluorophenoxy)ethyl]-1-piperidyl}ethyl)-3-phenyl-2-imidazolidinone and its Hydrochloride 7.72 mmol of the product of Preparation 2 and 7.72 mmol of the product of Preparation 23 are dissolved in 70 ml of methyl isobutyl ketone, and then 3.19 g of potassium carbonate are added. After reacting for 12 hours under reflux, the mixture is filtered and then evaporated. The residue is taken up in ethyl acetate and is then washed with ethyl acetate, dried, filtered and concentrated. Chromatography over silica gel (dichloro-methane/methanol/ammonium hydroxide: 95/5/0.5) allows the expected product to be isolated, which is converted into its hydrochloride using ethanolic hydrogen chloride solution.

| Melting point (M.K.): 176–180° C. Elemental microanalysis: | | | | |
|---|---|---|---|---|
| | C | H | N | Cl |
| % found | 64.27 | 7.05 | 9.27 | 8.28 |
| % calculated | 64.35 | 6.97 | 9.38 | 7.91 |

EXAMPLE 6

1-(2-{4-[2-(p-Fluorophenoxy)ethyl]-1-piperidyl}ethyl)-3-(p-methoxyphenyl)-2-imidazolidinone and its Hydrochloride The product is obtained according to the procedure of Example 5 using the product of Preparation 24 instead of that of Preparation 23.

| Melting point (M.K.): 197–203° C. Elemental microanalysis: | | | | |
|---|---|---|---|---|
| | C | H | N | Cl |
| % found | 62.78 | 7.17 | 8.82 | 7.82 |
| % calculated | 62.82 | 6.97 | 8.79 | 7.42 |

EXAMPLE 7

1-(2-{4-[2-(p-Fluorophenoxy)ethyl]-1-piperidyl}ethyl)-3-(p-hydroxyphenyl)-2-imidazolidinone and its Hydrochloride The product is obtained according to the procedure of Example 5 using the product of Preparation 25 instead of that of Preparation 23.

Melting point (M.K.): 201–206° C.
Elemental microanalysis:

|  | C | H | N | Cl |
|---|---|---|---|---|
| % found | 61.82 | 6.73 | 8.94 | 7.65 |
| % calculated | 62.13 | 6.73 | 9.06 | 7.64 |

EXAMPLE 8

1-(2-{4-[2-(p-Fluorophenoxy)ethyl]-1-piperidyl}ethyl)-3-(o-chlorophenoxy)-2-imidazolidinone and its Hydrochloride The product is obtained according to the procedure of Example 5 using the product of Preparation 26 instead of that of Preparation 23. The product is converted into the hydrochloride by the action of a solution of hydrochloric acid in acetonitrile.

Melting point (M.K.): 183–187° C.
Elemental microanalysis:

|  | C | H | N | Cl |
|---|---|---|---|---|
| % found | 59.70 | 6.23 | 8.74 | 14.89 |
| % calculated | 59.75 | 6.27 | 8.71 | 14.70 |

EXAMPLE 9

1-{2-[4-(Phenoxymethyl)-1-piperidyl]ethyl}-3-(p-hydroxyphenyl)-2-imidazolidinone and its Hydrochloride The product is obtained according to the procedure of Example 5 using the compounds of Preparations 3 and 25 as substrates. The product obtained is converted into its hydrochloride by the action of ethereal hydrogen chloride solution.

Melting point (M.K.): 260–263° C.
Elemental microanalysis:

|  | C | H | N | Cl |
|---|---|---|---|---|
| % found | 63.76 | 7.05 | 9.46 | 8.23 |
| % calculated | 63.95 | 7.00 | 9.73 | 8.23 |

EXAMPLE 10

1-{2-[4-(p-Fluorophenoxymethyl)-1-piperidyl]ethyl}-3-(p-methoxyphenyl)-2-imidazolidinone and its Hydrochloride The product is obtained according to the procedure of Example 5 using the compounds of Preparations 1 and 24 as substrates. The product obtained is converted into its hydrochloride by the action of ethereal hydrogen chloride solution.

Melting point (M.K.): 287–290° C.
Elemental microanalysis:

|  | C | H | N | Cl |
|---|---|---|---|---|
| % found | 62.28 | 6.93 | 9.02 | 7.81 |
| % calculated | 62.13 | 6.73 | 9.06 | 7.64 |

EXAMPLE 11

1-(2-{4-[2-(p-Fluorophenoxy)ethyl]-1-piperidyl}ethyl)-3-(p-fluorophenyl)-2-imidazolidinone and its Hydrochloride The product is obtained according to the procedure of Example 5 using the compounds of Preparations 2 and 27 as substrates. The product obtained is converted into its hydrochloride by the action of ethereal hydrogen chloride solution.

Melting point (M.K.): 174–178° C.
Elemental microanalysis:

|  | C | H | N | Cl |
|---|---|---|---|---|
| % found | 61.62 | 6.61 | 8.91 | 7.92 |
| % calculated | 61.86 | 6.49 | 9.02 | 7.61 |

EXAMPLE 12

1-{2-[4-(p-Fluorophenoxymethyl)-1-piperidyl]ethyl}-3-(p-benzyloxyphenyl)-2-imidazolidinone and its Hydrochloride The product is obtained according to the procedure of Example 5 using the compounds of Preparations 1 and 28 as substrates. The product obtained is converted into its hydrochloride by the action of ethereal hydrogen chloride solution.

Melting point (M.K.): 248–252° C.
Elemental microanalysis:

|  | C | H | N | Cl |
|---|---|---|---|---|
| % found | 66.76 | 6.49 | 7.72 | 6.75 |
| % calculated | 66.72 | 6.53 | 7.78 | 6.56 |

EXAMPLE 13

1-{2-[4-(p-Fluorophenoxymethyl)-1-piperidyl]ethyl}-3-(p-hydroxyphenyl)-2-imidazolidinone and its Hydrochloride The product is obtained according to the procedure of Example 5 using the compounds of Preparations 1 and 25 as substrates. The product obtained is converted into its hydrochloride by the action of ethereal hydrogen chloride solution.

Melting point (M.K.): 228–232° C.
Elemental microanalysis:

|  | C | H | N | Cl |
|---|---|---|---|---|
| % found | 61.38 | 6.43 | 9.40 | 8.01 |
| % calculated | 61.40 | 6.50 | 9.34 | 7.88 |

EXAMPLE 14

1-{2-[4-(p-Methylsulphonylphenoxymethyl)-1-piperidyl]-ethyl}-3-(p-hydroxyphenyl)-2-imidazolidinone and its Hydrochloride The product is obtained according to the procedure of Example 5 using the compounds of Preparations 4 and 25 as substrates. The product obtained is converted into its hydrochloride by the action of ethereal hydrogen chloride solution.

Melting point (M.K.): 265–270° C.
Elemental microanalysis:

|  | C | H | N | Cl |
|---|---|---|---|---|
| % found | 56.19 | 6.38 | 8.04 | 5.89 |
| % calculated | 56.52 | 6.32 | 8.24 | 6.29 |

EXAMPLE 15

1-(2-{4-[2-(p-Fluorophenoxy)ethyl]-1-piperidyl}ethyl) -3-(p-nitrophenyl)-2-imidazolidinone and its Hydrochloride The product is obtained according to the procedure of Example 5 using the compounds of Preparations 2 and 29 as substrates. The product obtained is precipitated in the form of its hydrochloride, which is recrystallised from acetonitrile.

Melting point (M.K.): 202–270° C.
Elemental microanalysis:

|  | C | H | N | Cl |
|---|---|---|---|---|
| % found | 58.55 | 6.12 | 11.34 | 7.19 |
| % calculated | 58.47 | 6.13 | 11.36 | 7.19 |

EXAMPLE 16

1-(2-{4-[2-(p-Fluorophenoxy)ethyl]-1-piperidyl}ethyl)-3-(p-chlorophenyl)-2-imidazolidinone and its Hydrochloride The product is obtained according to the procedure of Example 5 using the compounds of Preparations 2 and 30 as substrates. The product obtained is precipitated in the form of the hydrochloride, which is recrystallised from acetonitrile.

Melting point (M.K.): 180–184° C.
Elemental microanalysis:

|  | C | H | N | Cl |
|---|---|---|---|---|
| % found | 59.97 | 6.23 | 8.68 | 14.95 |
| % calculated | 59.75 | 6.27 | 8.71 | 14.70 |

EXAMPLE 17

1-{2-[4-(p-Fluorophenoxymethyl)-1-piperidyl]ethyl}-3-(p-nitrophenyl)-2-imidazolidinone and its Hydrochloride The product is obtained according to the procedure of Example 5 using the compounds of Preparations 1 and 29 as substrates. The product obtained is precipitated in the form of its hydrochloride and is recrystallised from acetonitrile.

Melting point (M.K.): 205–209° C.
Elemental microanalysis:

|  | C | H | N | Cl |
|---|---|---|---|---|
| % found | 57.83 | 5.89 | 11.60 | 6.87 |
| % calculated | 57.68 | 5.89 | 11.70 | 7.40 |

EXAMPLE 18

1-(2-{4-[2-(p-Methylsulphonylphenoxy)ethyl]-1-piperidyl}ethyl)-3-(p-hydroxyphenyl)-2-imidazolidinone and its Hydrochloride The product is obtained according to the procedure of Example 5 using the compounds of Preparations 5 and 25 as substrates. The product obtained is converted into its hydrochloride by the action of ethereal hydrogen chloride solution.

Melting point (M.K.): 120–125° C.
Elemental microanalysis:

|  | C | H | N | Cl | S |
|---|---|---|---|---|---|
| % found | 57.77 | 6.77 | 7.81 | 6.86 | 5.69 |
| % calculated | 57.30 | 6.54 | 8.02 | 6.76 | 6.12 |

EXAMPLE 19

1-{1-[2-(Benzofuran-3-yl)ethyl]-4-piperidyl}-3-phenyl-tetrahydro-2-pyrimidinone and its Hydrochloride Step 1: 1-{1-[2-(Benzofuran-3-yl)ethyl]-4-piperidyl}-4-hydroxy-3-phenyl-tetrahydro-2-pyrimidinone The product is obtained according to the procedure of Example 1, Steps 1 and 2, using the compound of Preparation 11 as substrate in Step 1.

Step 2: 1-{1-[2-(Benzofuran-3-yl)ethyl]-4-piperidyl}-3-phenyl-tetrahydro-2-pyrimidinone and its Hydrochloride 14.4 mmol of the compound obtained in the previous Step are hydrogenated at ambient temperature and atmospheric pressure in acetic acid in the presence of 10% Pd/C. After concentration, the residue is taken up in dichloromethane and sodium hydroxide solution. The organic phase is dried, filtered and then evaporated. The product obtained is converted into its hydrochloride by the action of ethanolic hydrogen chloride solution.

| Melting point (M.K.): 255–259° C. Elemental microanalysis: | | | | |
|---|---|---|---|---|
| | C | H | N | Cl |
| % found | 68.01 | 6.92 | 9.70 | 8.29 |
| % calculated | 68.25 | 6.87 | 9.55 | 8.06 |

EXAMPLE 20

1-{1-[3-(Benzofuran-3-yl)propyl]-4-piperidyl}-3-phenyl-tetrahydro-2-pyrimidinone and its Hydrochloride The product is obtained according to the procedure of Example 19 using the compound of Preparation 12 instead of that of Preparation 11 as substrate in Step 1. The product obtained is converted into its hydrochloride.

| Melting point (M.K.): 256–260° C. Elemental microanalysis: | | | | |
|---|---|---|---|---|
| | C | H | N | Cl |
| % found | 68.43 | 7.18 | 9.12 | 7.75 |
| % calculated | 68.78 | 7.10 | 9.26 | 7.81 |

EXAMPLE 21

1-(2-{4-[2-(p-Fluorophenoxy)ethyl]-1-piperidyl}ethyl)-3-phenyl-1,3-diazepan-2-one and its Hydrochloride Step 1: 1-(2-{4-[2-(p-Fluorophenoxy)ethyl]-1-piperidyl}ethyl)-3-phenylurea 11 mmol of the product of Preparation 17 dissolved in 10 ml of dichloromethane are poured onto 15 mmol of phenyl isocyanate dissolved in 6 ml of dichloromethane. After stirring for 16 hours at ambient temperature, the mixture is concentrated under reduced pressure. Chromatography over silica gel (dichloromethane/methanol/ammonium hydroxide: 95/5/0.5) allows the expected product to be isolated.

Melting point (K): 140° C.

Step 2: 1-(2-{4-[2-(p-Fluorophenoxy)ethyl]-1-piperidyl}ethyl)-3-phenyl-1,3-diazepan-2-one and its Hydrochloride To a solution of 9.7 mmol of the product obtained in Step 1 in 40 ml of dimethyl-formamide there are added, in portions, 3 equivalents of 60% sodium hydride. They are left in contact until no more gas is evolved; 2 equivalents of 1,4-dibromobutane are added and the mixture is heated at 80° C. for 4 hours and then left at ambient temperature for 12 hours. After evaporation, the residue is taken up in water and dichloromethane. The organic phase is washed with sodium hydroxide solution and then with water, and is dried, filtered and concentrated under reduced pressure. Chromatography over silica gel (dichloromethane/methanol/ammonium hydroxide: 95/5/0.5) allows the expected product to be isolated, which is converted into the hydrochloride, which is crystallised from acetonitrile.

| Melting point (M.K.): 170–175° C. Elemental microanalysis: | | | | |
|---|---|---|---|---|
| | C | H | N | Cl |
| % found | 65.22 | 7.37 | 8.74 | 8.07 |
| % calculated | 65.60 | 7.41 | 8.83 | 7.45 |

EXAMPLE 22

1-({1-[3-p-Fluorophenoxy)propyl]-4-piperidyl}methyl)-3-phenyl-1,3-diazepan-2-one and its Hydrochloride The product is obtained according to the procedure of Example 21 using the compound of Preparation 21 instead of that of Preparation 17 as substrate in Step 1. The product obtained is converted into its hydrochloride, which is crystallised from acetonitrile.

| Melting point (M.K.): 170–173° C. Elemental microanalysis: | | | | |
|---|---|---|---|---|
| | C | H | N | Cl |
| % found | 65.69 | 7.42 | 9.01 | 7.45 |
| % calculated | 65.60 | 7.41 | 8.83 | 7.45 |

EXAMPLE 23

1-{1-[2-(Benzofuran-3-yl)ethyl]-4-piperidyl}-3-phenyl-1,3-diazepan-2-one and its Hydrochloride The product is obtained according to the procedure of Example 21 using the compound of Preparation 7 instead of that of Preparation 17 as substrate in Step 1. The product obtained is converted into its hydrochloride by the action of ethereal hydrogen chloride solution.

| Melting point (M.K.): 232–237° C. Elemental microanalysis: | | | | |
|---|---|---|---|---|
| | C | H | N | Cl |
| % found | 69.34 | 7.23 | 9.18 | 8.07 |
| % calculated | 68.78 | 7.10 | 9.26 | 7.81 |

EXAMPLE 24

N-{1-[2-(p-Fluorophenoxy)ethyl]-4-piperidyl}indoline-carboxamide and its Hydrochloride Step 1: Indolin-1-ylcarbonyl chloride 22.5 mmol of diphosgene dissolved in 90 ml of dichloromethane are cooled to 0° C.; there are then added 45 mmol of indoline, and then 67.5 mmol of triethylamine, while maintaining the temperature at 0° C. After 12 hours at ambient temperature, the mixture is filtered and the filtrate is concentrated under reduced pressure.

Step 2: N-{1-[2-p-Fluorophenoxy)ethyl]-4-piperidyl}indolinecarboxamide and its Hydrochloride 12 mmol of the product obtained in Step 1 are added, in portions, to a solution of 12 mmol of the product of Preparation 22 and 36 mmol of diisopropylethylamine in 210 ml of dichloromethane. After 48 hours at ambient temperature, the mixture is diluted with water, separated, washed with water, dried, filtered and evaporated. Chromatography over silica gel (dichloromethane/ethanol: 95/5) allows the expected product to be isolated, which is converted into the hydrochloride in ethanolic hydrogen chloride.

Melting point: 228–235° C.
Elemental microanalysis:

|  | C | H | N | Cl |
|---|---|---|---|---|
| % found | 61.70 | 6.36 | 9.69 | 9.62 |
| % calculated | 61.85 | 6.43 | 9.84 | 9.96 |

EXAMPLE 25

N-{1-[3-(Benzofuran-3-yl)propyl]-4-piperidyl}-1-indoline-carboxamide and its Hydrochloride The product is obtained according to the procedure of Example 24 using the compound of Preparation 8 instead of that of Preparation 22 as substrate in Step 2. The product obtained is converted into its hydrochloride.

Melting point (M.K.): 253–257° C.
Elemental microanalysis:

|  | C | H | N | Cl |
|---|---|---|---|---|
| % found | 68.48 | 6.78 | 9.56 | 8.08 |
| % calculated | 68.25 | 6.87 | 9.55 | 8.06 |

EXAMPLE 26

N-{1-[2-(Benzofuran-3-yl)ethyl]-4-piperidyl}-1-indoline-carboxamide and its Hydrochloride The product is obtained according to the procedure of Example 24 using the compound of Preparation 7 instead of that of Preparation 22 as substrate in Step 2. The product obtained is converted into its hydrochloride by the action of ethereal hydrogen chloride solution.

Melting point (M.K.): 261–265° C.

Melting point (M.K.): 261–265° C.
Elemental microanalysis:

|  | C | H | N | Cl |
|---|---|---|---|---|
| % found | 67.71 | 6.67 | 9.81 | 8.77 |
| % calculated | 67.67 | 6.63 | 9.86 | 8.32 |

EXAMPLE 27

N-{1-[3-(Benzofuran-3-yl)propyl]-4-piperidyl}-1,2,3,4-tetrahydro-1-quinolinecarboxamide and its Hydrochloride The product is obtained according to the procedure of Example 24 using 1,2,3,4-tetra-hydroquinoline as substrate in Step 1 and, in Step 2, the product of Preparation 8 instead of that of Preparation 22. The product obtained is converted into its hydrochloride, which is recrystallised from ethanol.

Melting point (M.K.): 227–231° C.

Melting point (M.K.): 227–231° C.
Elemental microanalysis:

|  | C | H | N | Cl |
|---|---|---|---|---|
| % found | 69.13 | 7.13 | 9.26 | 7.79 |
| % calculated | 68.78 | 7.10 | 9.26 | 7.81 |

EXAMPLE 28

N-{1-[2-(Benzofuran-3-yl)ethyl]-4-piperidyl}-1,2,3,4-tetrahydro-1-quinolinecarboxamide and its Hydrochloride The product is obtained according to the procedure of Example 27 using the compound of Preparation 7 instead of that of Preparation 8 as substrate in Step 2. The product obtained is converted into its hydrochloride, which is recrystallised from ethanol.

Melting point (M.K.): 215–219° C.
Elemental microanalysis:

|  | C | H | N | Cl |
|---|---|---|---|---|
| % found | 68.27 | 6.85 | 9.44 | 8.26 |
| % calculated | 68.25 | 6.87 | 9.05 | 8.06 |

EXAMPLE 29

4-[2-(Benzofuran-3-yl)ethyl]-1-piperazinyl}-(2,3-dihydro-1H-indol-1-yl)methanone and its Hydrochloride The product is obtained according to the procedure of Example 24 using the compound of Preparation 13 instead of that of Preparation 22 as substrate in Step 2. The product obtained is converted into its hydrochloride by the action of ethereal hydrogen chloride solution.

Melting point (M.K.): 284–287° C.
Elemental microanalysis:

|  | C | H | N | Cl |
|---|---|---|---|---|
| % found | 67.27 | 6.51 | 10.21 | 8.43 |
| % calculated | 67.06 | 6.36 | 10.20 | 8.61 |

EXAMPLE 30

{4-[3-(Benzofuran-3-yl)propyl]-1-piperazinyl}-(2,3-dihydro-1H-indol-1-yl)methanone and its Hydrochloride The product is obtained according to the procedure of Example 24 using the compound of Preparation 14 instead of that of Preparation 22 as substrate in Step 2. The product obtained is converted into its hydrochloride and is recrystallised from acetonitrile.

| | Melting point (M.K.): 215–219° C. Elemental microanalysis: | | | |
|---|---|---|---|---|
| | C | H | N | Cl |
| % found | 67.69 | 6.62 | 9.89 | 7.69 |
| % calculated | 67.67 | 6.63 | 9.86 | 8.32 |

EXAMPLE 31

{1-[2-(p-Fluorophenoxy)ethyl]-4-piperazinyl}-(2,3-dihydro-1H-indol-1-yl)methanone and its Dihydrochloride The product is obtained according to the procedure of Example 24 using the compound of Preparation 15 instead of that of Preparation 22 as substrate in Step 2. The product obtained is converted into its hydrochloride and is recrystallised from acetonitrile.

| | Melting point (M.K.): 233–236° C. Elemental microanalysis: | | | |
|---|---|---|---|---|
| | C | H | N | Cl |
| % found | 62.48 | 6.26 | 10.30 | 8.85 |
| % calculated | 62.14 | 6.21 | 10.35 | 8.73 |

EXAMPLE 32

{1-[3-(p-Fluorophenoxy)propyl]-4-piperazinyl}-(2,3-dihydro-1H-indol-1-yl)methanone and its Hydrochloride The product is obtained according to the procedure of Example 24 using the compound of Preparation 16 instead of that of Preparation 22 as substrate in Step 2. The product obtained is converted into its hydrochloride, which is recrystallised from acetonitrile.

| | Melting point (M.K.): 250–254° C. Elemental microanalysis: | | | |
|---|---|---|---|---|
| | C | H | N | Cl |
| % found | 62.90 | 6.47 | 10.00 | 8.56 |
| % calculated | 62.93 | 6.48 | 10.01 | 8.44 |

EXAMPLE 33

N-(2-{4-[2-(p-Fluorophenoxy)ethyl]-1-piperidyl}ethyl)-1-indolinecarboxamide and its Hydrochloride The product is obtained according to the procedure of Example 24 using the compound of Preparation 17 instead of that of Preparation 22 as substrate in Step 2. The product obtained is converted into its hydrochloride.

| | Melting point (M.K.): 92–95° C. Elemental microanalysis: | | | |
|---|---|---|---|---|
| | C | H | N | Cl |
| % found | 64.16 | 7.36 | 9.18 | 8.15 |
| % calculated | 64.35 | 6.97 | 9.38 | 7.91 |

EXAMPLE 34

N-{2-[4-(p-Fluorophenoxymethyl)-1-piperidyl]ethyl}-1-indolinecarboxamide and its Hydrochloride The product is obtained according to the procedure of Example 24 using the compound of Preparation 18 instead of that of Preparation 22 as substrate in Step 2. The product obtained is converted into its hydrochloride, which is recrystallised from acetonitrile.

| | Melting point (M.K.): 143–145° C. Elemental microanalysis: | | | |
|---|---|---|---|---|
| | C | H | N | Cl |
| % found | 63.30 | 6.89 | 9.63 | 8.37 |
| % calculated | 63.66 | 6.74 | 9.68 | 8.17 |

EXAMPLE 35

N-{2-[4-(Phenoxymethyl)-1-piperidyl]ethyl}-1-indoline-carboxamide and its Hydrochloride The product is obtained according to the procedure of Example 24 using the compound of Preparation 19 instead of that of Preparation 22 as substrate in Step 2. The product obtained is converted into its hydrochloride, which is recrystallised from acetonitrile.

| | Melting point (M.K): 205–210° C. Elemental microanalysis: | | | |
|---|---|---|---|---|
| | C | H | N | Cl |
| % found | 65.93 | 7.29 | 9.97 | 8.87 |
| % calculated | 66.41 | 7.27 | 10.10 | 8.52 |

EXAMPLE 36

N-{2-[4-(p-Methylsulphonylphenoxymethyl)-1-piperidyl]-ethyl}-1-indolinecarboxamide and its Hydrochloride The product is obtained according to the procedure of Example 24 using the compound of Preparation 6 instead of that of Preparation 22 as substrate in Step 2. The product obtained is converted into its hydrochloride, which is recrystallised from acetonitrile.

| Melting point (M.K.): 199–203° C. Elemental microanalysis: | | | | |
|---|---|---|---|---|
| | C | H | N | Cl | S |
| % found | 58.54 | 6.64 | 8.56 | 7.25 | 6.32 |
| % calculated | 58.35 | 6.53 | 8.51 | 7.18 | 6.49 |

EXAMPLE 37

N-(2-{4-[(2-(Phenoxy)ethyl]-1-piperidyl}ethyl)-1-indoline-carboxamide and its Hydrochloride The product is obtained according to the procedure of Example 24 using the compound of Preparation 20 instead of that of Preparation 22 as substrate in Step 2. The product obtained is converted into its hydrochloride in ethanolic hydrogen chloride.

| Melting point (M.K.): 83–87° C. Elemental microanalysis: | | | | |
|---|---|---|---|---|
| | C | H | N | Cl |
| % found | 67.69 | 7.96 | 9.82 | 8.03 |
| % calculated | 67.04 | 7.50 | 9.77 | 8.25 |

EXAMPLE 38

N-{1-[2-(Benzofuran-3-yl)ethyl]-4-piperidyl}-1-indole-carboxamide and its Hydrochloride Step 1: (Imidazol-1-yl-indol-1-yl)methanone 90 mmol of carbonyldiimidazole and 0.24 g of 4-dimethylaminopyridine are added, in succession, to a solution of 85.4 mmol of indole in 305 ml of acetonitrile. After refluxing for 8 hours, the mixture is concentrated. The residue is taken up in a minimum of ether. After filtration, the expected product is obtained.

Step 2: N-{1-[2-(Benzofuran-3-yl)ethyl]-4-piperidyl}-1-indolecarboxamide and its Hydrochloride A solution of the product obtained in Step 1 and of the product of Preparation 7 in 25 ml of acetonitrile is heated at reflux for 12 hours. After cooling, the precipitate that forms is filtered off. The filtrate is concentrated, taken up in ethyl acetate and washed with water. The organic phase is dried, filtered and then concentrated under reduced pressure. Chromatography over silica gel (dichloromethane/ethanol: 95/5) allows the expected product to be isolated, which is converted into the hydrochloride using ethanolic hydrogen chloride solution.

| Melting point (M.K.): 275–280° C. Elemental microanalysis: | | | | |
|---|---|---|---|---|
| | C | H | N | Cl |
| % found | 67.96 | 6.14 | 9.82 | 8.34 |
| % calculated | 68.00 | 6.18 | 9.91 | 8.36 |

EXAMPLE 39

N-{2-[4-(p-Fluorophenoxymethyl)-1-piperidyl]ethyl}-1-indolecarboxamide and its Hydrochloride The product is obtained according to the procedure of Example 38 using the compound of Preparation 18 instead of that of Preparation 7 as substrate in Step 2. The product obtained is converted into its hydrochloride by the action of ethereal hydrogen chloride solution.

| Melting point (M.K.): 206–210° C. Elemental microanalysis: | | | | |
|---|---|---|---|---|
| | C | H | N | Cl |
| % found | 63.82 | 6.39 | 9.50 | 8.57 |
| % calculated | 63.96 | 6.30 | 9.73 | 8.21 |

EXAMPLE 40

N-(2-{4-[2-(p-Fluorophenoxy)ethyl]-1-piperidyl}ethyl)-1-indolecarboxamide and its Hydrochloride The product is obtained according to the procedure of Example 38 using the compound of Preparation 17 instead of that of Preparation 7 as substrate in Step 2. The product obtained is converted into its hydrochloride by the action of ethanolic hydrogen chloride solution.

| Melting point (M.K.): 214–218° C. Elemental microanalysis: | | | | |
|---|---|---|---|---|
| | C | H | N | Cl |
| % found | 64.60 | 6.55 | 9.38 | 7.99 |
| % calculated | 64.64 | 6.55 | 9.42 | 7.95 |

EXAMPLE 41

N-{2-[4-(Phenoxymethyl)-1-piperidyl]ethyl}-1-indole-carboxamide and its Hydrochloride The product is obtained according to the procedure of Example 38 using the compound of Preparation 19 instead of that of Preparation 7 as substrate in Step 2. The product obtained is converted into its hydrochloride.

| Melting point (M.K.): 171–174° C. Elemental microanalysis: | | | | |
|---|---|---|---|---|
| | C | H | N | Cl |
| % found | 66.41 | 6.88 | 10.01 | 8.85 |
| % calculated | 66.74 | 6.82 | 10.15 | 8.56 |

EXAMPLE 42

N-{2-[4-(Phenoxymethyl)-1-piperidyl]-ethyl}-5,6-dimethoxy-1-indolecarboxamide and its Hydrochloride The product is obtained according to the procedure of Example 38 using 5,6-dimethoxy-indole instead of indole in Step 1 and the product of Preparation 19 instead of that of Preparation 7 in Step 2. The product obtained is converted into its hydrochloride, which is crystallised from acetonitrile.

Melting point (M.K.): 204–208° C.

EXAMPLE 43

N-(2-{4-[2-(p-Fluorophenoxy)ethyl]-1-piperidyl}ethyl)-5-hydroxy-1-indolecarboxamide and its Hydrochloride Step 1: (5-Benzyloxyindol-1-yl-imidazol-1-yl)-methanone The product is obtained according to the procedure of Example 38, Step 1, using 5-benzyl-oxyindole instead of indole.

Step 2: N-(2-{4-[2-(Fluorophenoxy)ethyl]-1-piperidyl}ethyl)-5-benzyloxy-1-indolecarboxamide The product is obtained according to the procedure of Step 2 of Example 38 using the product of Preparation 17.

Step 3: N-(2-{4-[2-Fluorophenoxy)ethyl]-1-piperidyl}ethyl)-5-hydroxy-1-indolecarboxamide and its Hydrochloride 3.87 mmol of the product obtained in Step 2 in 150 ml of methanol are hydrogenated in the presence of 0.4 g of 10% Pd/C. After 4 hours at ambient temperature and atmospheric pressure, the mixture is concentrated under reduced pressure. Chromatography over silica gel (dichloromethane/ethanol: 95/5) allows the expected product to be isolated. The product is converted, by the action of ethereal hydrogen chloride solution, into its hydrochloride, which is crystallised from acetonitrile.

Melting point (M.K.): 237–241° C.

EXAMPLE 44

N-(2-{4-[2-(p-Fluorophenoxy)ethyl]-1-piperidyl}ethyl)-5-hydroxy-1-indolinecarboxamide and its Hydrochloride The product is obtained according to the procedure of Example 43 using 5-benzyl-oxyindoline as substrate in Step 1. The product obtained is converted into its hydrochloride by the action of ethereal hydrogen chloride solution.

Melting point (M.K.): 193–196° C.

EXAMPLE 45

N-{2-[4-(Phenoxymethyl)-1-piperidyl]ethyl}-5-fluoro-1-indolecarboxamide and its Hydrochloride Step 1: Bis(5-fluoroindol-1-yl)methanone 78.4 mmol of carbonyldiimidazole and 0.2 g of 4-dimethylaminopyridine are added to a solution of 74 mmol of 5-fluoroindole in 300 ml of acetonitrile. After refluxing for 8 hours, and then concentrating, the residue is taken up in a minimum of ether. The solidified product, which corresponds to the expected product, is filtered off.

Step 2: N-{2-[4-(Phenoxymethyl)-1-piperidyl]ethyl}-5-fluoro-1-indole-carboxamide and its Hydrochloride The product is obtained according to the procedure of Example 38 using, as substrate, the product obtained in Step 1 and the compound of Preparation 19 instead of that of Preparation 17. The product obtained is converted into its hydrochloride by the action of ethereal hydrogen chloride and is crystallised from acetonitrile.

Melting point (M.K.): 228–234° C.
Elemental microanalysis:

|  | C | H | N | Cl |
|---|---|---|---|---|
| % found | 64.04 | 6.32 | 9.71 | 7.88 |
| % calculated | 63.96 | 6.30 | 9.73 | 8.21 |

EXAMPLE 46

N-(2-{4-[2-(p-Fluorophenoxy)ethyl]-1-piperidyl}ethyl)-5-fluoro-1-indolecarboxamide and its Hydrochloride The product is obtained according to the procedure of Example 45 using the compound of Preparation 17 instead of that of Preparation 19 as substrate in Step 2. The product obtained is converted into its hydrochloride by the action of ethereal hydrogen chloride and is crystallised from isopropanol.

Melting point (M.K.): 205–209° C.
Elemental microanalysis:

|  | C | H | N | Cl |
|---|---|---|---|---|
| % found | 62.12 | 6.17 | 8.93 | 7.39 |
| % calculated | 62.13 | 6.08 | 9.06 | 7.64 |

EXAMPLE 47

N-{2-[4-(p-Fluorophenoxymethyl)-1-piperidyl]ethyl}-1-indolinesulphonamide and its Hydrochloride Step 1: 3-(2,3-Diltydroindol-1-ylsulphonyl)-1,3-oxazolidin-2-one 7.1 ml of 2-bromoethanol in 50 ml of dichloromethane are added to a solution of 8.72 ml of chlorosulphonyl isocyanate in 40 ml of dichloromethane. The resulting solution is then added, at 0° C., to a solution of 11.23 ml of indoline and 15.46 ml of triethylamine in 200 ml of dichloromethane. After stirring for 24 hours at ambient temperature, 10N hydrochloric acid is added. The organic phase is then washed with hydrochloric acid and then with water, and is dried, filtered and concentrated, allowing the expected product to be obtained.

Step 2: N-(2-Hydroxyethyl)-1-indolinesulphonamide

The product of Step 1 is dissolved in a solution of 3.2 g of sodium hydroxide in 80 ml of ethanol. After stirring for 48 hours at ambient temperature, the mixture is filtered. The filtrate is concentrated under reduced pressure, taken up in dichloromethane and washed with water. After drying and filtration, the organic phase is concentrated under reduced pressure, allowing the expected product to be obtained.

Step 3: N-(2-Bromoethyl)-1-indolinesulphonamide 3.5 g of the product previously obtained are refluxed for 12 hours in the presence of a mixture of 4.54 g of triphenylphosphine, 5.72 g of carbon tetrabromide and 73.5 ml of ethyl ether. The reaction mixture is then concentrated under reduced pressure and chromatography over silica gel (dichloromethane/ethyl acetate: 95/5) allows the expected product to be isolated.

Step 4: N-{2-[4-(p-Fluorophenoxymethyl)-1-piperidyl]ethyl}-1-indoline-sulphonamide and its Hydrochloride A solution containing 1.5 g of the product previously obtained, 1.2 g of the product of Preparation 1, 1.5 g of sodium carbonate and 20 ml of acetone is refluxed for 12 hours and then concentrated. The residue is taken up in dichloromethane and washed with water; the organic phase is then dried, filtered and evaporated. Chromatography over silica gel (dichloromethane/ethanol: 98/2) allows the expected product to be isolated, which is converted into its hydrochloride by the action of ethereal hydrogen chloride solution.

| Melting point (M.K.): 151–155° C. Elemental microanalysis: | | | | | |
|---|---|---|---|---|---|
| | C | H | N | Cl | S |
| % found | 56.12 | 6.22 | 8.72 | 7.77 | 6.67 |
| % calculated | 56.22 | 6.22 | 8.94 | 7.54 | 6.82 |

EXAMPLE 48

N-(2-{4-[2-(p-Fluorophenoxy)ethyl]-1-piperidyl}ethyl)-1-indolinesulphonamide and its Hydrochloride The product is obtained according to the procedure of Example 47 using the compound of Preparation 2 instead of that of Preparation 1 as substrate in Step 4. The product obtained is converted into its hydrochloride.

| Melting point (M.K.): 137–141° C. Elemental microanalysis: | | | | | |
|---|---|---|---|---|---|
| | C | H | N | Cl | S |
| % found | 56.43 | 6.54 | 8.44 | 7.22 | 6.28 |
| % calculated | 57.07 | 6.46 | 8.68 | 7.32 | 6.62 |

EXAMPLE 49

1-(4-Fluorophenyl)-3-{2-[4-(phenoxymethyl)-1-piperidyl]-ethyl}-2-imidazolidinone and its Hydrochloride The product is obtained according to the procedure of Example 5 using the compounds of Preparations 3 and 27 as substrates. The product is converted into its hydrochloride by the action of ethereal hydrogen chloride solution.

| Melting point (M.K.): 239–243° C. Elemental microanalysis: | | | | |
|---|---|---|---|---|
| | C | H | N | Cl |
| % found | 63.75 | 6.79 | 9.57 | 8.37 |
| % calculated | 63.65 | 6.74 | 9.69 | 8.17 |

EXAMPLE 50

1-(2-{4-[2-(4-Chlorophenoxy)ethyl]-1-piperidyl}ethyl)-3-(4-fluorophenyl)-2-imidazolidinone and its Hydrochloride The product is obtained according to the procedure of Example 5 using the compounds of Preparations 31 and 27 as substrates. The product is converted into its hydrochloride by the action of ethereal hydrogen chloride solution.

| Melting point (M.K.): 189–193° C. Elemental microanalysis: | | | | |
|---|---|---|---|---|
| | C | H | N | Cl |
| % found | 59.31 | 6.12 | 8.61 | 14.74 |
| % calculated | 59.75 | 6.27 | 8.71 | 14.70 |

EXAMPLE 51

1-(4-Fluorophenyl)-3-[2-(4-{[4-(methylthio)phenoxy]-methyl}-1-piperidyl)ethyl]-2-imidazolidinone and its Hydrochloride The product is obtained according to the procedure of Example 5 using the compounds of Preparations 32 and 27 as substrates. The product is converted into its hydrochloride by the action of ethereal hydrogen chloride solution.

| Melting point (M.K.): 240–245° C. Elemental microanalysis: | | | | | |
|---|---|---|---|---|---|
| | C | H | N | Cl | S |
| % found | 60.07 | 6.64 | 8.62 | 7.71 | 6.72 |
| % calculated | 60.05 | 6.51 | 8.75 | 7.39 | 6.68 |

EXAMPLE 52

1-(4-Fluorophenyl)-3-[2-(4-{2-[4-(methylthio)phenoxy]-ethyl}-1-piperidyl)ethyl]-2-imidazolidinone and its Hydrochloride The product is obtained according to the procedure of Example 5 using the compounds of Preparations 33 and 27 as substrates. The product is converted into its hydrochloride by the action of ethereal hydrogen chloride solution.

| Melting point (M.K.): 218–223° C. Elemental microanalysis: | | | | | |
|---|---|---|---|---|---|
| | C | H | N | Cl | S |
| % found | 61.28 | 6.88 | 8.62 | 7.31 | 6.06 |
| % calculated | 60.77 | 6.73 | 8.51 | 7.18 | 6.49 |

EXAMPLE 53

1-(4-Chlorophenyl)-3-{2-[4-(phenoxymethyl)-1-piperidyl]-ethyl}-2-imidazolidinone and its Hydrochloride The product is obtained according to the procedure of Example 5 using the compounds of Preparations 3 and 30 as substrates. The product is converted into its hydrochloride by the action of ethereal hydrogen chloride solution.

| Melting point (M.K.): 277–282° C. Elemental microanalysis: | | | |
|---|---|---|---|
| C | H | N | Cl |
| % found 61.67 | 6.34 | 9.33 | 15.94 |
| % calculated 61.33 | 6.49 | 9.33 | 15.74 |

EXAMPLE 54

1-(4-Chlorophenyl)-3-{2-[4-(2-phenoxyethyl)-1-piperidyl]-ethyl}-2-imidazolidinone and its Hydrochloride The product is obtained according to the procedure of Example 5 using the compounds of Preparations 34 and 30 as substrates. The product is converted into its hydrochloride by the action of ethereal hydrogen chloride solution.

| Melting point (M.K.): 215–219° C. Elemental microanalysis: | | | |
|---|---|---|---|
| C | H | N | Cl |
| % found 62.07 | 6.73 | 8.98 | 14.47 |
| % calculated 62.07 | 6.68 | 9.05 | 15.27 |

EXAMPLE 55

1-(2-{4-[2-(4-Chlorophenoxy)ethyl]-1-piperidyl}ethyl)-3-(4-chlorophenyl)-2-imidazolidinone and its Hydrochloride The product is obtained according to the procedure of Example 5 using the compounds of Preparations 31 and 30 as substrates. The product is converted into its hydrochloride by the action of ethereal hydrogen chloride solution.

| Melting point (M.K.): 200–205° C. Elemental microanalysis: | | | |
|---|---|---|---|
| C | H | N | Cl |
| % found 57.97 | 5.94 | 8.45 | 21.52 |
| % calculated 57.78 | 6.06 | 8.42 | 21.32 |

EXAMPLE 56

1-(4-Chlorophenyl)-3-(2-{4-[(4-fluorophenoxy)methyl]-1-piperidyl}ethyl)-2-imidazolidinone and its Hydrochloride The product is obtained according to the procedure of Example 5 using the compounds of Preparations 1 and 30 as substrates. The product is converted into its hydrochloride by the action of ethereal hydrogen chloride solution.

| Melting point (M.K.): 218–222° C. Elemental microanalysis: | | | |
|---|---|---|---|
| C | H | N | Cl |
| % found 58.91 | 5.97 | 8.82 | 15.37 |
| % calculated 58.97 | 6.03 | 8.97 | 15.14 |

EXAMPLE 57

1-(4-Chlorophenyl)-3-[2-(4-{[4-(methylthio)phenoxy]-methyl}-1-piperidyl)ethyl]-2-imidazolidinone and its Hydrochloride The product is obtained according to the procedure of Example 5 using the compounds of Preparations 32 and 30 as substrates. The product is converted into its hydrochloride by the action of ethereal hydrogen chloride solution.

| Melting point (M.K.): 288–292° C. Elemental microanalysis: | | | | |
|---|---|---|---|---|
| C | H | N | Cl | S |
| % found 58.26 | 6.40 | 8.41 | 14.38 | 6.69 |
| % calculated 58.06 | 6.29 | 8.46 | 14.28 | 6.46 |

EXAMPLE 58

1-(4-Nitrophenyl)-3-{2-[4-(phenoxymethyl)-1-piperidyl]-ethyl}-2-imidazolidinone and its Hydrochloride The product is obtained according to the procedure of Example 5 using the compounds of Preparations 3 and 29 as substrates. The product is converted into its hydrochloride by the action of ethereal hydrogen chloride solution.

| Melting point (M.K.): 216–220° C. Elemental microanalysis: | | | |
|---|---|---|---|
| C | H | N | Cl |
| % found 59.51 | 6.36 | 11.98 | 7.82 |
| % calculated 59.93 | 6.34 | 12.15 | 7.69 |

EXAMPLE 59

1-[2-(4-{[4-(Methylthio)phenoxy]methyl}-1-piperidyl)-ethyl]-3-(4-nitrophenyl)-2-imidazolidinone and its Hydrochloride The product is obtained according to the procedure of Example 5 using the compounds of Preparations 32 and 29 as substrates. The product is converted into its hydrochloride by the action of ethereal hydrogen chloride solution.

| | Melting point (M.K.): 243–247° C. Elemental microanalysis: | | | | |
|---|---|---|---|---|---|
| | C | H | N | Cl | S |
| % found | 56.57 | 6.09 | 10.83 | 6.91 | 5.99 |
| % calculated | 56.85 | 6.16 | 11.05 | 6.99 | 6.32 |

EXAMPLE 60

1-(2-{4-[2-(4-Chlorophenoxy)ethyl]-1-piperidyl}ethyl)-3-(4-nitrophenyl)-2-imidazolidinone and its Hydrochloride The product is obtained according to the procedure of Example 5 using the compounds of Preparations 31 and 29 as substrates. The product is converted into its hydrochloride by the action of ethereal hydrogen chloride solution.

| | Melting point (M.K.): 196–201° C. Elemental microanalysis: | | | |
|---|---|---|---|---|
| | C | H | N | Cl |
| % found | 57.02 | 5.88 | 10.91 | 14.26 |
| % calculated | 56.59 | 5.94 | 11.00 | 13.92 |

EXAMPLE 61

1-(4-Hydroxyphenyl)-3-[2-(4-{[4-(methylthio)phenoxy]-methyl}-1-piperidyl)ethyl]-2-imidazolidinone and its Hydrochloride The product is obtained according to the procedure of Example 5 using the compounds of Preparations 32 and 25 as substrates. The product is converted into its hydrochloride by the action of ethereal hydrogen chloride solution.

| | Melting point (M.K.): 273–277° C. Elemental microanalysis: | | | | |
|---|---|---|---|---|---|
| | C | H | N | Cl | S |
| % found | 60.07 | 6.72 | 8.78 | 7.09 | 6.34 |
| % calculated | 60.30 | 6.75 | 8.79 | 7.42 | 6.71 |

EXAMPLE 62

1-{2-[4-(Phenoxymethyl)-1-piperidyl]ethyl}-3-[4-(trifluoro-methyl)phenyl]-2-imidazolidinone and its Hydrochloride The product is obtained according to the procedure of Example 5 using the compounds of Preparations 3 and 35 as substrates. The product is converted into its hydrochloride by the action of ethereal hydrogen chloride solution.

| | Melting point (M.K.): 224–228° C. Elemental microanalysis: | | | |
|---|---|---|---|---|
| | C | H | N | Cl |
| % found | 59.70 | 6.12 | 8.66 | 7.46 |
| % calculated | 59.56 | 6.04 | 8.68 | 7.33 |

EXAMPLE 63

4-(2-Oxo-3-{2-[4-(phenoxymethyl)-1-piperidyl]ethyl}-1-imidazolidinyl)benzonitrile and its Hydrochloride The product is obtained according to the procedure of Example 5 using the compounds of Preparations 3 and 36 as substrates. The product is converted into its hydrochloride by the action of ethereal hydrogen chloride solution.

| | Melting point (M.K.): 210–215° C. Elemental microanalysis: | | | |
|---|---|---|---|---|
| | C | H | N | Cl |
| % found | 64.82 | 6.63 | 12.23 | 7.74 |
| % calculated | 65.37 | 6.63 | 12.71 | 8.04 |

EXAMPLE 64

1-(4-Fluoro-3-nitrophenyl)-3-(2-{4-[2-(4-fluorophenoxy)ethyl]-1-piperidyl}ethyl)-1,3-dihydro-2H-imidazol-2-one and its Hydrochloride The product is obtained according to the procedure of Example 1, Steps 1 and 2, using the compound of Preparation 37 and 4-fluoro-3-nitrophenyl isocyanate as substrates. The product is converted into its hydrochloride by the action of ethereal hydrogen chloride solution.

| | Melting point (M.K.): 205–209° C. Elemental microanalysis: | | | |
|---|---|---|---|---|
| | C | H | N | Cl |
| % found | 56.58 | 5.23 | 10.95 | 7.06 |
| % calculated | 56.64 | 5.35 | 11.01 | 6.97 |

EXAMPLE 65

1-[2-(1,1-Dioxo-5-phenyl-1,2,5-thiadiazolidin-2-yl)ethyl]-4-(phenoxymethyl)piperidine and its Hydrochloride The product is obtained according to the procedure of Example 5 using the compounds of Preparations 3 and 38 as substrates. The product is converted into its hydrochloride by the action of ethereal hydrogen chloride solution.

| Melting point (M.K.): 198–202° C. | | | | |
|---|---|---|---|---|
| Elemental microanalysis: | | | | |
| C | H | N | Cl | S |
| % found      59.01 | 6.81 | 9.37 | 8.19 | 7.06 |
| % calculated 58.46 | 6.69 | 9.30 | 7.84 | 7.09 |

EXAMPLE 66

1-{2-[5-(4-Chlorophenyl)-1,1-dioxo-1,2,5-thiadiazolidin-2-yl]-ethyl}-4-(phenoxymethyl)piperidine and its Hydrochloride The product is obtained according to the procedure of Example 5 using the compounds of Preparations 3 and 39 as substrates. The product is converted into its hydrochloride by the action of ethereal hydrogen chloride solution.

| Melting point (M.K.): 189–194° C. | | | | |
|---|---|---|---|---|
| Elemental microanalysis: | | | | |
| C | H | N | Cl | S |
| % found      54.27 | 5.94 | 8.47 | 15.12 | 6.49 |
| % calculated 54.32 | 6.01 | 8.64 | 14.58 | 6.59 |

EXAMPLE 67

1-{2-[5-(4-Fluorophenyl)-1,1-dioxo-1,2,5-thiadiazolidin-2-yl]-ethyl}-4-(phenoxymethyl)piperidine and its Hydrochloride The product is obtained according to the procedure of Example 5 using the compounds of Preparations 3 and 40 as substrates. The product is converted into its hydrochloride by the action of ethereal hydrogen chloride solution.

| Melting point (M.K.): 195–200° C. | | | | |
|---|---|---|---|---|
| Elemental microanalysis: | | | | |
| C | H | N | Cl | S |
| % found      56.57 | 6.25 | 9.02 | 7.51 | 6.73 |
| % calculated 56.22 | 6.22 | 8.94 | 7.54 | 6.82 |

EXAMPLE 68

1-{2-[5-(4-Chlorophenyl)-1,1-dioxo-1,2,5-thiadiazolidin-2-yl]-ethyl}-4-[2-(4-fluorophenoxy)ethyl]piperidine and its Hydrochloride The product is obtained according to the procedure of Example 5 using the compounds of Preparations 2 and 39 as substrates. The product is converted into its hydrochloride by the action of ethereal hydrogen chloride solution.

| Melting point (M.K): 195–199° C. | | | | |
|---|---|---|---|---|
| Elemental microanalysis: | | | | |
| C | H | N | Cl | S |
| % found      53.34 | 5.91 | 8.12 | 13.76 | 6.28 |
| % calculated 53.28 | 5.83 | 8.10 | 13.68 | 6.18 |

EXAMPLE 69

6-Fluoro-N-(2-{4-[(4-fluorophenoxy)methyl]-1-piperidyl}ethyl)-1H-indole-1-carboxamide and its Hydrochloride The product is obtained according to the procedure of Example 45, Steps 1 and 2, using, as substrate in Step 1, 6-fluoroindole instead of 5-fluoroindole and, in Step 2, the compound of Preparation 18. The product is converted into its hydrochloride by the action of ethereal hydrogen chloride solution.

| Melting point (M.K.): 180–184° C. | | | |
|---|---|---|---|
| Elemental microanalysis: | | | |
| C | H | N | Cl |
| % found      61.27 | 5.77 | 9.34 | 8.23 |
| % calculated 61.40 | 5.82 | 9.34 | 7.88 |

EXAMPLE 70

6-Fluoro-N-(2-{4-[2-(4-fluorophenoxy)ethyl]-1-piperidyl}-ethyl)-1H-indole-1-carboxamide and its Hydrochloride The product is obtained according to the procedure of Example 45, Steps 1 and 2, using, as substrate in Step 1, 6-fluoroindole instead of 5-fluoroindole and, in Step 2, the compound of Preparation 17. The product is converted into its hydrochloride by the action of ethereal hydrogen chloride solution.

| Melting point (M.K.): 185–190° C. | | | |
|---|---|---|---|
| Elemental microanalysis: | | | |
| C | H | N | Cl |
| % found      61.99 | 6.08 | 9.01 | 7.75 |
| % calculated 62.13 | 6.08 | 9.06 | 7.64 |

EXAMPLE 71

6-Chloro-N-{2-[4-(phenoxymethyl)-1-piperidyl]ethyl}-1H-indole-1-carboxamide and its Hydrochloride The product is obtained according to the procedure of Example 45, Steps 1 and 2, using, as substrate in Step 1, 6-chloroindole instead of 5-fluoroindole and, in Step 2, the compound of Preparation 19. The product is converted into its hydrochloride by the action of ethereal hydrogen chloride solution.

| | Melting point (M.K): 211–215° C. | | | |
|---|---|---|---|---|
| | Elemental microanalysis: | | | |
| | C | H | N | Cl |
| % found | 61.72 | 6.13 | 9.39 | 15.91 |
| % calculated | 61.61 | 6.07 | 9.37 | 15.81 |

EXAMPLE 72

6-Chloro-N-(2-{4-[2-(4-fluorophenoxy)ethyl]-1-piperidyl}-ethyl)-1H-indole-1-carboxamide and its Hydrochloride The product is obtained according to the procedure of Example 45, Steps 1 and 2, using, as substrate in Step 1, 6-chloroindole instead of 5-fluoroindole and, in Step 2, the compound of Preparation 17. The product is converted into its hydrochloride by the action of ethereal hydrogen chloride solution.

| | Melting point (M.K.): 176–180° C. | | | |
|---|---|---|---|---|
| | Elemental microanalysis: | | | |
| | C | H | N | Cl |
| % found | 60.36 | 5.99 | 8.61 | 14.98 |
| % calculated | 60.00 | 5.87 | 8.75 | 14.76 |

EXAMPLE 73

5-Chloro-N-{2-[4-(phenoxymethyl)-1-piperidyl]ethyl}-1H-indole-1-carboxamide and its Hydrochloride The product is obtained according to the procedure of Example 45, Steps 1 and 2, using, as substrate in Step 1, 5-chloroindole instead of 5-fluoroindole and, in Step 2, the compound of Preparation 19. The product is converted into its hydrochloride by the action of ethereal hydrogen chloride solution.

| | Melting point (M.K.): 187–190° C. | | | |
|---|---|---|---|---|
| | Elemental microanalysis: | | | |
| | C | H | N | Cl |
| % found | 61.82 | 6.12 | 9.35 | 15.54 |
| % calculated | 61.61 | 6.07 | 9.37 | 15.81 |

EXAMPLE 74

6-Methoxy-N-{2-[4-phenoxymethyl)-1-piperidyl]ethyl}-1H-indole-1-carboxamide and its Hydrochloride The product is obtained according to the procedure of Example 38, Steps 1 and 2, using, as substrate in Step 1, 6-methoxyindole and, in Step 2, the compound of Preparation 19. The product is converted into its hydrochloride by the action of ethereal hydrogen chloride solution.

| | Melting point (M.K.): 201–207° C. | | | |
|---|---|---|---|---|
| | Elemental microanalysis: | | | |
| | C | H | N | Cl |
| % found | 64.96 | 6.87 | 9.33 | 8.19 |
| % calculated | 64.93 | 6.81 | 9.46 | 7.99 |

EXAMPLE 75

5-Methoxy-N-{2-[4-(phenoxymethyl)-1-piperidyl]ethyl}-1H-indole-1-carboxamide and its Hydrochloride The product is obtained according to the procedure of Example 38, Steps 1 and 2, using, as substrate in Step 1, 5-methoxyindole and, in Step 2, the compound of Preparation 19. The product is converted into its hydrochloride by the action of ethereal hydrogen chloride solution.

| | Melting point (M.K.): 178–182° C. | | | |
|---|---|---|---|---|
| | Elemental microanalysis: | | | |
| | C | H | N | Cl |
| % found | 65.12 | 7.00 | 9.48 | 8.02 |
| % calculated | 64.93 | 6.81 | 9.46 | 7.99 |

EXAMPLE 76

N-(2-{4-[(4-Fluorophenoxy)methyl]-1-piperidyl}ethyl)-5-methoxy-1H-indole-1-carboxamide and its Hydrochloride The product is obtained according to the procedure of Example 38, Steps 1 and 2, using, as substrate in Step 1, 5-methoxyindole and, in Step 2, the compound of Preparation 18. The product is converted into its hydrochloride by the action of ethereal hydrogen chloride solution.

| | Melting point (M.K.): 186–191° C. | | | |
|---|---|---|---|---|
| | Elemental microanalysis: | | | |
| | C | H | N | Cl |
| % found | 62.38 | 6.41 | 8.90 | 8.10 |
| % calculated | 62.40 | 6.33 | 9.10 | 7.67 |

EXAMPLE 77

N-(2-{4-[2-(4-Fluorophenoxy)ethyl]-1-piperidyl}ethyl)-5-methoxy-1H-indole-1-carboxamide and its Hydrochloride The product is obtained according to the procedure of Example 38, Steps 1 and 2, using, as substrate in Step 1, 5-methoxyindole and, in Step 2, the compound of Preparation 17. The product is converted into its hydrochloride by the action of ethereal hydrogen chloride solution.

|  | Melting point (M.K.):203–207° C. Elemental microanalysis: | | | |
|---|---|---|---|---|
|  | C | H | N | Cl |
| % found | 63.02 | 6.46 | 8.78 | 7.43 |
| % calculated | 63.08 | 6.56 | 8.83 | 7.45 |

EXAMPLE 78

5-Hydroxy-N-{2-[4-(phenoxymethyl)-1-piperidyl]ethyl}-1H-indole-1-carboxamide and its Hydrochloride The product is obtained according to the procedure of Example 43, Steps 1 to 3, using the compound of Preparation 19 as substrate in Step 2. The product is converted into its hydrochloride by the action of ethereal hydrogen chloride solution.

|  | Melting point (M.K.):210–214° C. Elemental microanalysis: | | | |
|---|---|---|---|---|
|  | C | H | N | Cl |
| % found | 64.42 | 6.73 | 9.86 | 8.54 |
| % calculated | 64.25 | 6.56 | 9.77 | 8.25 |

EXAMPLE 79

5-Chloro-N-{2-[4-(phenoxymethyl)-1-piperidyl]ethyl}-1-indolinecarboxamide and its Hydrochloride The product is obtained according to the procedure of Example 24, Steps 1 and 2, using, as substrate in Step 1, 5-chloroindoline and, in Step 2, the compound of Preparation 19. The product is converted into its hydrochloride by the action of ethereal hydrogen chloride solution.

|  | Melting point (M.K.):128–132° C. Elemental microanalysis: | | | |
|---|---|---|---|---|
|  | C | H | N | Cl |
| % found | 61.16 | 6.53 | 9.25 | 7.44 |
| % calculated | 61.33 | 6.49 | 9.33 | 7.87 |

EXAMPLE 80

6-Chloro-N-(2-{4-[2-(4-fluorophenoxy)ethyl]-1-piperidyl}-ethyl)-1-indolinecarboxamide and its Hydrochloride The product is obtained according to the procedure of Example 24, Steps 1 and 2, using, as substrate in Step 1, 6-chloroindoline and, in Step 2, the compound of Preparation 17. The product is converted into its hydrochloride by the action of ethereal hydrogen chloride solution.

|  | Melting point (M.K.):153–156° C. Elemental microanalysis: | | | |
|---|---|---|---|---|
|  | C | H | N | Cl |
| % found | 59.38 | 6.31 | 8.66 | 14.57 |
| % calculated | 59.75 | 6.27 | 8.71 | 14.70 |

EXAMPLE 81

5-Fluoro-N-(2-{4-[2-(4-fluorophenoxy)ethyl]-1-piperidyl}-ethyl)-1-indolinecarboxamide and its Hydrochloride The product is obtained according to the procedure of Example 24, Steps 1 and 2, using, as substrate in Step 1, 5-fluoroindoline and, in Step 2, the compound of Preparation 17. The product is converted into its hydrochloride by the action of ethereal hydrogen chloride solution.

|  | Melting point (M.K.):185–189° C. Elemental microanalysis: | | | |
|---|---|---|---|---|
|  | C | H | N | Cl |
| % found | 62.19 | 6.71 | 8.83 | 7.86 |
| % calculated | 61.86 | 6.49 | 9.02 | 7.61 |

EXAMPLE 82

6-Fluoro-N-{2-[4phenoxymethyl)-1-piperidyl]ethyl}-1-indolinecarboxamide and its Hydrochloride The product is obtained according to the procedure of Example 24, Steps 1 and 2, using, as substrate in Step 1, 6-fluoroindoline and, in Step 2, the compound of Preparation 19. The product is converted into its hydrochloride by the action of ethereal hydrogen chloride solution.

|  | Melting point (M.K.):168–172° C. Elemental microanalysis: | | | |
|---|---|---|---|---|
|  | C | H | N | Cl |
| % found | 63.34 | 6.73 | 9.55 | 8.80 |
| % calculated | 63.66 | 6.74 | 9.68 | 8.17 |

EXAMPLE 83

5-Fluoro-N-{2-[4-(phenoxymethyl)-1-piperidyl]ethyl}-1-indolinecarboxamide and its Hydrochloride The product is obtained according to the procedure of Example 24, Steps 1 and 2, using, as substrate in Step 1, 5-fluoroindoline and, in Step 2, the compound of Preparation 19. The product is converted into its hydrochloride by the action of ethereal hydrogen chloride solution.

| Melting point (M.K.):168–171° C. Elemental microanalysis: | | | | |
|---|---|---|---|---|
| | C | H | N | Cl |
| % found | 63.65 | 6.98 | 9.58 | 7.99 |
| % calculated | 63.66 | 6.74 | 9.68 | 8.17 |

EXAMPLE 84

5-Methoxy-N-{2-[4-(phenoxymethyl)-1-piperidyl]ethyl}-1-indolinecarboxamide and its Hydrochloride The product is obtained according to the procedure of Example 24, Steps 1 and 2, using, as substrate in Step 1, 5-methoxyindoline and, in Step 2, the compound of Preparation 19. The product is converted into its hydrochloride by the action of ethereal hydrogen chloride solution.

| Melting point (M.K.):193–196° C. Elemental microanalysis: | | | | |
|---|---|---|---|---|
| | C | H | N | Cl |
| % found | 64.55 | 7.00 | 9.30 | 8.46 |
| % calculated | 64.64 | 7.29 | 9.42 | 7.95 |

EXAMPLE 85

5-Methoxy-N-[2-(4-{[4-(methylthio)phenoxy]methyl}-1-piperidyl)ethyl]-1-indolinecarboxamide and its Hydrochloride The product is obtained according to the procedure of Example 24, Steps 1 and 2, using, as substrate in Step 1, 5-methoxyindoline and, in Step 2, the compound of Preparation 41. The product is converted into its hydrochloride by the action of ethereal hydrogen chloride solution.

| Melting point (M.K.): 201–205° C. Elemental microanalysis: | | | | | |
|---|---|---|---|---|---|
| | C | H | N | Cl | S |
| % found | 60.96 | 7.15 | 8.45 | 7.59 | 6.53 |
| % calculated | 61.02 | 6.96 | 8.54 | 7.20 | 6.52 |

EXAMPLE 86

N-[2-(4-{[4-(Methylthio)phenoxy]methyl}-1-piperidyl)ethyl]-1-indolinecarboxamide and its Hydrochloride The product is obtained according to the procedure of Example 24, Steps 1 and 2, using, as substrate in Step 1, indoline and, in Step 2, the compound of Preparation 41. The product is converted into its hydrochloride by the action of ethereal hydrogen chloride solution.

| Melting point (M.K.): 165–170° C. Elemental microanalysis: | | | | | |
|---|---|---|---|---|---|
| | C | H | N | Cl | S |
| % found | 63.11 | 7.15 | 9.05 | 7.96 | 6.92 |
| % calculated | 62.39 | 6.98 | 9.09 | 7.67 | 6.94 |

EXAMPLE 87

5-Nitro-N-{2-[4-(phenoxymethyl)-1-piperidyl]ethyl}-1-indolinecarboxamide and its Hydrochloride The product is obtained according to the procedure of Example 24, Steps 1 and 2, using, as substrate in Step 1, 5-nitroindoline and, in Step 2, the compound of Preparation 19. The product is converted into its hydrochloride by the action of ethereal hydrogen chloride solution.

| Melting point (M.K.):210–220° C. Elemental microanalysis: | | | | |
|---|---|---|---|---|
| | C | H | N | Cl |
| % found | 59.86 | 6.27 | 12.01 | 8.10 |
| % calculated | 59.93 | 6.34 | 12.15 | 7.69 |

EXAMPLE 88

N-(2-{4-[2-(4-Fluorophenoxy)ethyl]-1-piperidyl}ethyl)-5-nitro-1-indolinecarboxamide and its Hydrochloride The product is obtained according to the procedure of Example 24, Steps 1 and 2, using, as substrate in Step 1, 5-nitroindoline and, in Step 2, the compound of Preparation 17. The product is converted into its hydrochloride by the action of ethereal hydrogen chloride solution.

| Melting point (M.K.): 205–210° C. Elemental microanalysis: | | | | |
|---|---|---|---|---|
| | C | H | N | Cl |
| % found | 58.22 | 6.15 | 11.25 | 7.85 |
| % calculated | 58.47 | 6.13 | 11.36 | 7.19 |

EXAMPLE 89

5,6-Dimethoxy-N-{2-[4-(phenoxymethyl)-1-piperidyl]ethyl}-1-indolinecarboxamide and its Hydrochloride The product of Example 42 is subjected to hydrogenation under the conditions described in Step 3 of Example 43, allowing the expected product to be isolated, which is converted into its hydrochloride in conventional manner.

| Melting point (M.K.): 118–122° C. Elemental microanalysis: | | | | |
|---|---|---|---|---|
| | C | H | N | Cl |
| % found | 63.50 | 7.39 | 8.79 | 7.71 |
| % calculated | 63.08 | 7.20 | 8.83 | 7.45 |

EXAMPLE 90

N-{2-[4-(Phenoxymethyl)-1-piperidyl]ethyl}-6,7-dihydro-5H-[1,3]dioxolo[4,5f]-indole-5-carboxamide and its Hydrochloride The product is obtained according to the procedure of Example 24, Steps 1 and 2, using, as substrate in Step 1, 5,6-methylenedioxyindoline and, in Step 2, the compound of Preparation 19. The product is converted into its hydrochloride by the action of ethereal hydrogen chloride solution.

| Melting point (M.K.):215–219° C. Elemental microanalysis: | | | | |
|---|---|---|---|---|
| | C | H | N | Cl |
| % found | 62.80 | 6.56 | 9.05 | 8.03 |
| % calculated | 62.67 | 6.57 | 9.14 | 7.71 |

EXAMPLE 91

N-(2-{4-[2-(4-Fluorophenoxy)ethyl]-1-piperidyl}ethyl)-1,3-dihydro-2H-isoindole-2-carboxamide and its Hydrochloride The product is obtained according to the procedure of Example 24, Steps 1 and 2, using, as substrate in Step 1, isoindoline and, in Step 2, the compound of Preparation 17. The product is converted into its hydrochloride by the action of ethereal hydrogen chloride solution.

| Melting point (M.K.): 175–179° C. Elemental microanalysis: | | | | |
|---|---|---|---|---|
| | C | H | N | Cl |
| % found | 63.78 | 6.93 | 9.22 | 7.85 |
| % calculated | 64.35 | 6.97 | 9.38 | 7.91 |

EXAMPLE 92

N-{2-[4-(Phenoxymethyl)-1-piperidyl]ethyl}-1,3-dihydro-2H-isoindole-2-carboxamide and its Hydrochloride The product is obtained according to the procedure of Example 24, Steps 1 and 2, using, as substrate in Step 1, isoindoline and, in Step 2, the compound of Preparation 19. The product is converted into its hydrochloride by the action of ethereal hydrogen chloride solution.

| Melting point (M.K.): 178–181° C. Elemental microanalysis: | | | | |
|---|---|---|---|---|
| | C | H | N | Cl |
| % found | 66.03 | 7.26 | 10.00 | 8.57 |
| % calculated | 66.41 | 7.27 | 10.10 | 8.52 |

EXAMPLE 93

N-{2-[4-(Phenoxymethyl)-1-piperidyl]ethyl}-1,2,3,4-tetrahydroisoquinolinecarboxamide and its Hemi-Fumarate The product is obtained according to the procedure of Example 24, Steps 1 and 2, using, as substrate in Step 1, 1,2,3,4-tetrahydroisoquinoline and, in Step 2, the compound of Preparation 19. The product is converted into its hemi-fumarate.

| Melting point (M.K.): 150–154° C. Elemental microanalysis: | | | |
|---|---|---|---|
| | C | H | N |
| % found | 68.34 | 7.35 | 9.01 |
| % calculated | 68.45 | 7.28 | 9.07 |

EXAMPLE 94

6,7-Dimethoxy-N-{2-[4-(phenoxymethyl-1-piperidyl]ethyl}-1,2,3,4-tetrahydroisoquinolinecarboxamide and its Fumarate The product is obtained according to the procedure of Example 24, Steps 1 and 2, using, as substrate in Step 1, 6,7-dimethoxy-1,2,3,4-tetrahydroisoquinoline and, in Step 2, the compound of Preparation 19. The product is converted into its fumarate.

| Melting point (M.K.): 200–205° C. Elemental microanalysis: | | | |
|---|---|---|---|
| | C | H | N |
| % found | 62.70 | 6.71 | 7.22 |
| % calculated | 63.25 | 6.90 | 7.38 |

EXAMPLE 95

5-Hydroxy-N-{2-[4-(phenoxymethyl)-1-piperidyl]ethyl}-1-indolinecarboxamide and its Hydrochloride The product is obtained according to the procedure of Example 43, Steps 1 to 3, using the compound of Preparation 19 as substrate in Step 2. The product is converted into its hydrochloride by the action of ethereal hydrogen chloride solution.

|  | Melting point (M.K.): 198–202° C. Elemental microanalysis: | | | |
|---|---|---|---|---|
|  | C | H | N | Cl |
| % found | 63.80 | 7.33 | 9.64 | 8.38 |
| % calculated | 63.95 | 7.00 | 9.73 | 8.21 |

EXAMPLE 96

5-Hydroxy-N-methyl-N-{2-[4-(phenoxymethyl)-1-piperidyl]-ethyl}-1-indolinecarboxamide and its Hydrochloride The product is obtained according to the procedure of Example 43, Steps 1 to 3, using the compound of Preparation 42 as substrate in Step 2. The product is converted into its hydrochloride by the action of ethereal hydrogen chloride solution.

|  | Melting point (M.K.): 105–110° C. Elemental microanalysis: | | | |
|---|---|---|---|---|
|  | C | H | N | Cl |
| % found | 64.74 | 7.34 | 9.32 | 8.19 |
| % calculated | 64.63 | 7.23 | 9.20 | 7.95 |

EXAMPLE 97

N-(2-{4-[2-(1-Benzofuran-3-yl)ethyl]-1-piperazinyl}ethyl)-1-indolinecarboxamide and its Hydrochloride The product is obtained according to the procedure of Example 24, Steps 1 and 2, using, as substrate in Step 1, indoline and, in Step 2, the compound of Preparation 43. The product is converted into its hydrochloride by the action of ethereal hydrogen chloride solution.

|  | Melting point (M.K.): 195–199° C. Elemental microanalysis: | | | |
|---|---|---|---|---|
|  | C | H | N | Cl |
| % found | 61.40 | 6.43 | 11.26 | 14.66 |
| % calculated | 61.10 | 6.56 | 11.40 | 14.43 |

EXAMPLE 98

N-{2-[4-(Phenoxymethyl)-1-piperidyl]ethyl}-1-indoline-sulphonamide and its Hydrochloride The product is obtained according to the procedure of Example 47, Steps 1 to 4, using the compound of Preparation 3 as substrate in Step 4. The product is converted into its hydrochloride by the action of ethereal hydrogen chloride solution.

|  | Melting point (M.K.): 168–172° C. Elemental microanalysis: | | | | |
|---|---|---|---|---|---|
|  | C | H | N | Cl | S |
| % found | 58.31 | 6.79 | 9.23 | 8.05 | 6.98 |
| % calculated | 58.46 | 6.69 | 9.30 | 7.84 | 7.09 |

EXAMPLE 99

N-{2-[4-(2-Phenoxyethyl)-1-piperidyl]ethyl}-1-indoline-sulphonamide and its Hydrochloride The product is obtained according to the procedure of Example 47, Steps 1 to 4, using the compound of Preparation 34 as substrate in Step 4. The product is converted into its hydrochloride by the action of ethereal hydrogen chloride solution.

|  | Melting point (M.K.): 133–135° C. Elemental microanalysis: | | | | |
|---|---|---|---|---|---|
|  | C | H | N | Cl | S |
| % found | 59.12 | 6.99 | 8.96 | 7.75 | 7.09 |
| % calculated | 59.28 | 6.92 | 9.02 | 7.61 | 6.88 |

EXAMPLE 100

5-Fluoro-N-{2-[4-(phenoxymethyl)-1-piperidyl]ethyl}-1-indolinesulphonamide and its Hydrochloride The product is obtained according to the procedure of Example 47, Steps 1 to 4, using, as substrate in Step 1, 5-fluoroindoline instead of indoline and, in Step 4, the compound of Preparation 3. The product is converted into its hydrochloride by the action of ethereal hydrogen chloride solution.

|  | Melting point (M.K.): 173–176° C. Elemental microanalysis: | | | | |
|---|---|---|---|---|---|
|  | C | H | N | Cl | S |
| % found | 56.80 | 6.38 | 9.12 | 7.77 | 6.66 |
| % calculated | 56.22 | 6.22 | 8.94 | 7.54 | 6.82 |

EXAMPLE 101

6-Chloro-N-(2-{4-[2-(phenoxy)methyl]-1-piperidyl}ethyl)-1-indolinecarboxamide and its Hydrochloride The product is obtained according to the procedure of Example 24, Steps 1 and 2, using, as substrate in Step 1, 6-chloroindoline and, in Step 2, the compound of Preparation 19. The product is converted into its hydrochloride by the action of ethereal hydrogen chloride solution.

| | Melting point (M.K.): 175–179° C. Elemental microanalysis: | | | |
|---|---|---|---|---|
| | C | H | N | Cl |
| % found | 61.32 | 6.58 | 9.32 | 16.53 |
| % calculated | 61.33 | 6.49 | 9.33 | 15.74 |

EXAMPLE 102

5-Fluoro-N-(2-{4-[2-(4-fluorophenoxy)ethyl]-1-piperazinyl}-ethyl)-1-indolinecarboxamide and its Dihydrochloride The product is obtained according to the procedure of Example 24, Steps 1 and 2, using, as substrate in Step 1, 5-fluororoindoline and, in Step 2, the compound of Preparation 44. The product is converted into its dihydrochloride.

| | Melting point (M.K.): 179–184° C. Elemental microanalysis: | | | |
|---|---|---|---|---|
| | C | H | N | Cl |
| % found | 54.67 | 5.89 | 11.18 | 14.16 |
| % calculated | 54.88 | 6.01 | 11.13 | 14.08 |

EXAMPLE 103

N-{2-[4-(Phenoxymethyl)-1-piperidyl]ethyl}-6-fluoro-1-indolecarboxamide and its Hydrochloride The product is obtained according to the procedure of Example 38, Steps 1 and 2, but using, in Step 1, 6-fluoroindole instead of indole and, in Step 2, the product of Preparation 19.

Melting point (M.K.): 184–188° C.

EXAMPLE 104

N-Methyl-N-{2-[4-(phenoxymethyl)-1-piperidyl] ethyl}-5,6-dimethoxy-1-indolinecarboxamide and its Hydrochloride This product is obtained according to the procedure of Example 24, Steps 1 and 2, using, as substrate in Step 1, 5,6-dimethoxyindoline and, in Step 2, the compound of Preparation 42.

Melting point (M.K.): 84–87° C.

EXAMPLE 105

N-{2-[4-(Phenoxymethyl)-1-piperidyl]ethyl}-4,5,6-trimethoxy-1-indolecarboxamide and its Hydrochloride The product is obtained according to the procedure of Example 38, Steps 1 and 2, but using, in Step 1, 4,5,6-trimethoxyindole instead of indole and, in Step 2, the product of Preparation 19.

Melting point (M.K.): 217–220° C.

EXAMPLE 106

N-{2-[4-(Phenoxymethyl)-1-piperidyl]ethyl}-4,5,6-trimethoxy-1-indolinecarboxamide and its Hydrochloride The product is obtained according to the procedure of Example 24, Steps 1 and 2, but using, in Step 1, 4,5,6-trimethoxyindoline and, in Step 2, the product of Preparation 19.

Melting point (M.K.): 147–151° C.

EXAMPLE 107

1-(4-Fluorophenyl)-3-(2-{4-[2-(phenoxy)ethyl]-1-piperidyl}-ethyl)-2-imidazolidinone and its Hydrochloride The product is obtained according to the procedure of Example 5, using the compounds of Preparations 34 and 27. The product is converted into its hydrochloride by the action of ethereal hydrogen chloride solution.

Melting point (M.K.): 176–179° C.

EXAMPLE 108

1-(4-Nitrophenyl)-3-(2-{4-[2-(phenoxy)ethyl]-1-piperidyl}-ethyl)-2-imidazolidinone and its Hydrochloride The product is obtained according to the procedure of Example 5, using the compounds of Preparations 34 and 29. The product is converted into its hydrochloride by the action of ethereal hydrogen chloride solution.

Melting point (M.K.): 197–202° C.

EXAMPLE 109

1-{2-[4-(Phenoxymethyl)-1-piperidyl]ethyl}-3-phenyl-2-imidazolidinone and its Hydrochloride The product is obtained according to the procedure of Example 5, using the compound of Preparation 3 instead of that of Preparation 2. The product is converted into its hydrochloride by the action of ethereal hydrogen chloride solution.

Melting point (M.K.): 214–218° C.

EXAMPLE 110

N-{2-[4-(Phenoxymethyl)-1-piperidyl]ethyl}-5-methoxy-pyrrolo[2,3-c]pyridine-1-carboxamide and its Dihydrochloride The product is obtained according to the procedure of Example 45, Steps 1 and 2, using, as substrate in Step 1, the product of Preparation 45 instead of 5-fluoroindole. The product is converted into its dihydrochloride by the action of ethereal hydrogen chloride solution.

Melting point (M.K.): 190–195° C.

Pharmacological Study of Compounds of the Invention

Under standard in vitro conditions, relaxation of aortic rings caused by acetylcholine (ACh), which relaxation is entirely dependent on the presence of endothelium, is the reflection of the production of NO (stimulated by ACh), which by diffusing to smooth muscle cells brings about arterial relaxation (*Nature,* 1980, 288, 373).

The compounds of the invention were tested in respect of two models involving two different mechanisms implicated in the endothelial dysfunction observed in pathology:

the first model consists of causing inhibition of the relaxation due to ACh by blocking the enzymatic activity (endothelial NOS) responsible for the production of NO;

the second model consists of causing oxidative stress in vitro using an enzymatic system that generates $O_2$ (xanthine oxidase—XO and hypoxanthine—Hypo).

EXAMPLE 111

Vascular Protective Effects with Respect to Endothelial Dysfunction Caused by an Inhibitor of NOS The thoracic aorta of a Wistar rat (325–375 g), anaesthetised by the intraperitoneal route using pentobarbital sodium (30 mg/kg), is removed and dissected into rings having a length of 3 mm. Each ring is suspended from an isometric tension sensor connected to a recording system and the initial tension applied is 2.5 g. The physiological solution used, which is thermostatically maintained at 37° C. and oxygenated (95% $O_2$+5% $CO_2$), comprises (in mM): NaCl 112.0; KCl 5.0; $CaCl_2$ 2.5; $KH_2PO_4$ 1.0; $MgSO_4$ 1.2; $NaHCO_3$ 25.0; glucose 11.5; Ca-EDTA 0.016.

After a 90-minute stabilisation period, the preparations are contracted using phenylephrine (PHE $10^{-6}$ M) and relaxed by adding $10^{-5}$ M of acetylcholine in order to verify the integrity of the endothelial layer. If that is confirmed, the preparations are rinsed and a concentration of the product under test is added to the medium followed by $3 \times 10^{-7}$ M of $N^G$-nitro-L-arginine (LNA). The preparations are again contracted using phenylephrine and, after 30 minutes, the relaxations due to acetylcholine (ACh—$10^{-8}$ M to $10^{-5}$ M) are assessed in the presence of indomethacin ($10^{-5}$ M).

The relaxation values are expressed as a percentage relative to the maximum contraction caused by PHE. The protective effects of the compounds with respect to the endothelial dysfunction correspond to the difference between the percentages of maximum relaxation observed in the presence or absence of product.

By way of example, the compound of Example 35 at $10^{-8}$, $3 \times 10^{-8}$ and $10^{-7}$ M inhibits, by 8, 26 and 29%, respectively, the endothelial dysfunction caused by LNA.

EXAMPLE 112

Protective Vascular Effects with Respect to Endothelial Dysfunction Caused by a System Generating $O_2^-$ This protocol, carried out on aortic rings of New Zealand rabbits (2.5–3 kg), is comparable to the previous protocol except for the following points: the initial tension applied is 5 g and the combination XO (3 mU/ml)-Hypo ($10^{-4}$ M) is used instead of the LNA.

By way of example, the compound of Example 35 at $3 \times 10^{-8}$ M inhibits by 17% the endothelial dysfunction caused by the XO-Hypo combination.

EXAMPLE 113

Inovolvement of NO in the Vascular Protective Effects Detected: Assessment of Aortic Production of cGMP By diffusing to the smooth muscle cells, the NO produced by the endothelial cells activates soluble guanylate cyclase, which brings about an increase in cyclic GMP, which is responsible for relaxation.

The content of that mediator in rat aortic rings was therefore determined in order to demonstrate that the protective effects of the compounds with respect to endothelial dysfunction are mediated by an increase in the availability of NO.

The rat aortic rings are prepared as previously. The effects of 30-minute incubation of compounds of the invention at different concentrations are assessed on the production of cGMP stimulated by ACh ($10^{-5}$ M—1 minute) in the presence of LNA ($3 \times 10^{-6}$ M). The said experiments are carried out in the presence of isobutylmethylxanthine ($10^{-5}$ M) in order to avoid degradation of the cGMP by phosphodiesterases. The rings are frozen in liquid nitrogen and maintained at −80° C. until the assay is carried out. The cGMP content is assessed by radioimmunoassay and expressed in relation to the amount of proteins contained in the tissue (assay by the Bradford method).

By way of example, the compound of Example 35, at $10^{-7}$ M, increases by 28.1% the production of cGMP stimulated by ACh in the presence of LNA.

EXAMPLE 114

Pharmaceutical Composition—Tablet

Formulation for the preparation of 1000 tablets each containing 10 mg of active ingredient

| | |
|---|---|
| Compound of Example 35 | 10 g |
| Hydroxypropyl cellulose | 2 g |
| Polyvinylpyrrolidone | 2 g |
| Wheat starch | 10 g |
| Lactose | 100 g |
| Magnesium stearate | 3 g |

We claim:

1. A compound selected from those of formula (I):

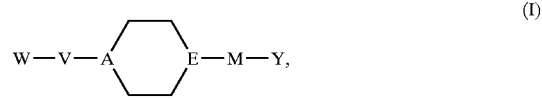

(I)

wherein:

V represents a single bond or a linear or branched $(C_1-C_6)$alkylene chain,

M represents a single bond or a linear or branched $(C_1-C_6)$alkylene chain,

A and E each represents nitrogen or CH, but at least one of the two group A or E represents nitrogen, W represents a group of formula (ii), or may also represent a group of formula (iii) provided that V represents a single bond and A represents nitrogen, in which groups of formulae (ii) and (iii):

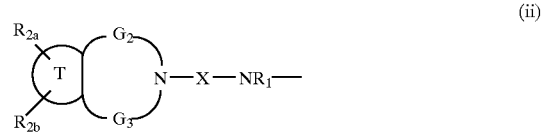

(ii)

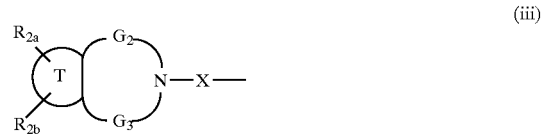

(iii)

X represents carbonyl, sulphonyl or sulphoxide, $G_2$ represents a single bond or methylene, $G_3$ represents:

a linear $C_3$ alkylene chain when $C_2$ represents a bond, or a linear $C_2$ alkylene chain when $G_2$ represents methylene, the alkylene chain in each of those cases optionally containing a double bond, T represents phenyl fused with the ring to which it is attached, R₁ represents hydrogen, linear or branched (C₁–C₆)alkyl, aryl or aryl-(C₁–C₆)alkyl in which the alkyl moiety is linear or branched, R$_{2a}$ and R$_{2b}$, which are the same or different, each independently of the other represents a group selected from hydrogen, halogen, linear or branched (C₁–C₆) alkyl, hydroxy, linear or branched (C₁–C₆)alkoxy, mercapto, linear or branched (C₁–C₆)alkylthio, linear or branched (C₁–C₆)trihaloalkyl, cyano, nitro, amino, linear or branched (C₁–C₆)alkylamino, di-(C₁–C₆) alkylamino in which each alkyl moiety may be linear or branched, linear or branched (C₁–C₆)trihaloalkoxy, aryloxy, aryl-(C₁–C₆)alkoxy in which the alkoxy moiety is linear or branched, linear or branched (C₁–C₆) alkylsulphonate, linear or branched (C₁–C₆) trihaloalkylsulphonate and linear or branched (C₁–C₆) alkylsulphonyl, or R$_{2a}$+R$_{2b}$, taken together in adjacent positions, represent a group selected from methylenedioxy, 1,2-ethylenedioxy, 1,3-propylenedioxy, and ethylene optionally substituted by a group selected from cyano, hydroxymethyl, linear or branched (C₁–C₆) alkoxycarbonyl, aryloxycarbonyl and aryl-(C₁–C₆) alkoxycarbonyl in which the alkoxy moiety is linear or branched, Y represents aryloxy, heteroaxyl-A-oxy or heteroaryl-B, each of which groups may optionally be substituted by one or more groups, which may be the same or different, selected from among the definitions of R$_{2a}$, its isomers, its hydrates, its solvates and addition salts thereof with a pharmaceutically acceptable acid, wherein:

aryl is understood to mean a group selected from phenyl, biphenyl, naphthyl, dihydronaphthyl, tetrahydronaphthyl, indanyl, indenyl and benzocyclobutyl, heteroaryl-A is understood to mean a monocyclic aromatic or bicyclic, 5- to 12-membered system containing one or two hetero atoms, which may be the same or different, selected from oxygen, nitrogen and sulphur, and wherein, in the vase of a bicyclic system, one of the rings has an aromatic character and the other ring may be aromatic or partially hydrogenated, heteroaryl-B is understood to mean a monocyclic aromatic or bicyclic aromatic, 5- to 12-membered system containing from 1 to 3 hetero atoms, which may be the same or different, selected from oxygen, nitrogen and sulphur, aryloxy is understood to mean aryl as defined hereinbefore attached to oxygen, heteroaryl-A-oxy is understood to mean heteroaryl-A as defined hereinbefore attached to an oxygen atom.

2. A compound of claim 1, wherein Y represents benzofuran-3-yl or phenyloxy optionally substituted by a group R$_{2a}$.

3. A compound of claim 1, wherein X represents carbonyl.

4. A compound of claim 1, wherein W represents a group of formula (ii).

5. A compound of claim 1, which is a compound of formula (IB):

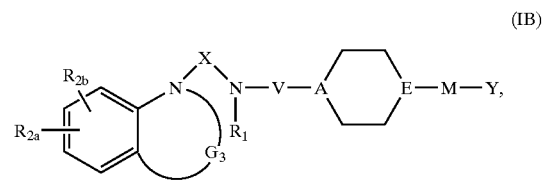

(IB)

wherein:

R$_{2a}$ and R$_{2b}$ are as defined for formula (I),

G₃ represents a group of formula —(CH₂)₃—,

X represents carbonyl,

R₁ represents hydrogen,

A, E and V are as defined for formula (I),

M represents a linear or branched (C₁–C₄)alkylene chain,

Y represents benzofuran-3-yl, or phenyloxy optionally substituted by a group selected from halogen, linear or branched (C₁–C₆)alkylsulphonyl and linear or branched (C₁–C₆)alkylthio.

6. A compound of claim 5, wherein:

A represents nitrogen and E represents CH when Y represents an optionally substituted phenyloxy group, or A represents CH and E represents nitrogen when Y represents benzofuran-3-yl.

7. A compound of claim 5, wherein:

V represents a single bond when Y represents benzofuran-3-yl, or V represents a linear or branched (C₁–C₄)alkylene chain when Y represents optionally substituted phenyloxy.

8. A compound of claim 1, wherein W represents a group of formula (iii).

9. A method for treating a living animal body afflicted with a disease or pathological condition which is associated with endothelial dysfunction, including atherosclerosis; vascular risk factors including dislipidaemia, diabetes, and systemic arterial hypertension; myocardial or peripheral ischaemia; cardiac insufficiency; pulmonary aterial hypertension; development, extension, and complications of atherosclerotic lesions; and vascular complications related a vascular bypass, vascular dilatation, vascular repermeabilisation and/or heart transplantation, comprising the step of administering to the living animal body an amount of a compound of claim 1 which is effective for alleviation of said disease or condition.

10. A pharmaceutical composition comprising as active principle an effective amount of a compound of claim 1, together with one or more inert, non-toxic pharmaceutically acceptable excipients or vehicles.

11. A method for treating a living animal body afflicted with myocardial or peripheral ischaemia, cardiac insufficiency or pulmonary arterial hypertension, comprising the step of administering to the living body an amount of a compound of claim 1 which is effective for alleviation of said conditions.

12. A method for treating a living animal body afflicted with a condition associated with the development, extension and complications of atherosclerotic lesions, or vascular complications after vascular bypass, vascular dilatation, vascular repermeabilisation and heart transplantation, comprising the step of administering to the living animal body an amount of a compound of claim 1 which is effective for alleviation of said condition.

13. A method for treating a living animal body having a vascular risk factor, including dyslipidaemia, diabetes, and/or systemic arterial hypertension, afflicted with a condition associated with the development, extension and complications of atherosclerotic lesions or vascular complications after vascular bypass, vascular dilatation, vascular repermeabilisation and heart transplantation, comprising the step of administering to the living animal body an amount of a compound of claim 1 which is effective for alleviation of said condition.

* * * * *

UNITED STATES PATENT AND TRADEMARK OFFICE
CERTIFICATE OF CORRECTION

PATENT NO. : 6,903,103 B2
DATED : June 7, 2005
INVENTOR(S) : Jean-Louis Peglion et al.

It is certified that error appears in the above-identified patent and that said Letters Patent is hereby corrected as shown below:

<u>Title page,</u>
Item [73], Assignee, "Les Laboratories Servier" should be -- Les Laboratoires Servier --.

<u>Column 59,</u>
Line 17, "tribaloalkoxy" should be -- trihaloalkoxy --.

Signed and Sealed this

Eleventh Day of October , 2005

JON W. DUDAS
*Director of the United States Patent and Trademark Office*